(12) United States Patent
Georges

(10) Patent No.: US 7,176,035 B2
(45) Date of Patent: Feb. 13, 2007

(54) PROTEIN-PROTEIN INTERACTIONS AND METHODS FOR IDENTIFYING INTERACTING PROTEINS AND THE AMINO ACID SEQUENCE AT THE SITE OF INTERACTION

(75) Inventor: Elias Georges, 2095 rue de Vouvray, Chomedey, Laval (CA) H7M 3J7

(73) Assignee: Elias Georges, Laval (CA)

( * ) Notice: Subject to any disclaimer, the term of this patent is extended or adjusted under 35 U.S.C. 154(b) by 265 days.

(21) Appl. No.: 10/010,310

(22) Filed: Nov. 13, 2001

(65) Prior Publication Data

US 2002/0142348 A1    Oct. 3, 2002

Related U.S. Application Data

(63) Continuation of application No. PCT/CA00/00587, filed on May 12, 2000.

(60) Provisional application No. 60/134,259, filed on May 14, 1999.

(51) Int. Cl.
*G01N 33/557*   (2006.01)

(52) U.S. Cl. ............... 436/517; 436/503; 436/507; 436/517; 436/518; 436/524; 436/528; 436/538; 436/87; 436/89; 435/6; 435/7.1; 435/7.2

(58) Field of Classification Search ............... 436/518, 436/528, 531, 532, 543, 89, 503, 507, 517, 436/524, 538, 87; 435/6, 7.92, 7.1, 7.2; 530/333, 530/334

See application file for complete search history.

(56) References Cited

U.S. PATENT DOCUMENTS 5,595,915 A * 1/1997 Geysen ............... 436/518

2004/0180386 A1 * 9/2004 Carr et al. ............... 435/7.21

FOREIGN PATENT DOCUMENTS

| EP | 0 818 467 | 1/1998 | |
| EP | 0818467 A2 * | 1/1998 | ............... 436/523 |

(Continued)

OTHER PUBLICATIONS

Burns et al., Glycoprotein-88 (CD36) Binds Tubulin and Endogenous Thrombospondin, Journal of Cellular Biochemistry, (Mar. 29, 1993) Supp. 17E, pp. 158. ☐☐*

(Continued)

*Primary Examiner*—Gailene R. Gabel
*Assistant Examiner*—Marissa Butler
(74) *Attorney, Agent, or Firm*—Wilmer Cutler Pickering Hale and Dorr

(57) ABSTRACT

The invention relates to protein-protein interactions and methods for identifying interacting proteins and the amino acid sequence at the site of interaction. Using overlapping hexapeptides that encode for the entire amino acid sequences of the linker domains of human P-glycoprotein gene 1 and 3 (HP-gp1 and HP-gp3), a direct and specific binding between HP-gp1 and 3 linker domains and intracellular proteins was demonstrated. The method of the present invention was further validated with Annexin. The present invention thus demonstrates a novel concept whereby the interactions between two proteins are mediated by strings of few amino acids with high and repulsive binding energies, enabling the identification of high affinity binding sites between any interacting proteins.

24 Claims, 16 Drawing Sheets

FOREIGN PATENT DOCUMENTS

| | | |
|---|---|---|
| WO | WO 84 03564 | 9/1984 |
| WO | WO 96/41469 | 12/1996 |
| WO | WO 98 15833 | 4/1998 |
| WO | WO 99/21980 | 5/1999 |

OTHER PUBLICATIONS

Georges et al., Topology of P-glycoprotein as determined by epitope mapping of MRK-16 Monoclonal Antibody, The Journal of Biological Chemistry 263 (3): 1792-1798 (1993)).*
Georges et al. (1990) "Detection of P-glycoprotein Isoforms By Gene-Specific Monoclonal Antibodies," 87 *Proc. Natl. Acad. Sci. USA* 152-156.
Georges et al. (1993) "Topology of P-Glycoprotein as Determined By Epitope Mapping of MRK-16 Monoclonal Antibody," 268(3) *J. Biol. Chem.* 1792-1798.
Cianfriglia et al. (1995) "P-Glycoprotein Epitope Mapping II The Murine Monoclonal Antibody MM6.15 to Human Multidrug-Resistant Cells Bind With Three Distinct Loops in the MDR1-P-Glycoprotein Extracellular Domain," 61 *Cancer* 142-147.
PCT/CA00/00587 International Preliminary Examination Report dated Jul. 26, 2001.
Lowry et al. (1951) "Protein Measurement with the Folin Phenol Reagent," 193 *J. Biol. Chem.* 265-275.
Edman et al. (1967) "A Protein Sequenator," 1 *Eur. J. Biochem.* 80-91.
Laemmli (1970) "Cleavage of Structural Proteins During the Assembly of the Head of Bacteriophase T4," 227 *Nature* 680-685.
Venter et al. (1972) "Shotgun Sequencing of the Human Genome," 280 *Science* 1540-1542.
Vincent et al. (1972) "Trypsin-Pancreatic Trypsin Inhibitor Association. Dynamics of the Interaction and Role of Disulfide Bridges," 11 *Biochemistry* 2967-2977.
Klotz et al. (1975) "Quaternary Structure of Proteins," *The Proteins* Neurath and Hill (eds.), Academic Press, Inc., NY pp. 293-411.
Tschesche et al. (1975) The Amino-Acid Sequence of Isoinhibitor K from Snails (*Helix pomalia*) 58 *Eur. J. Biochem.* 439-451.
Steitz et al. (1977) "High Resolution Crystal Structures of Yeast Hexokinase Complexes with Substrates, Activators, and Inhibitors," 252 *J. Biol. Chem.* 4494-4500.
Towbin et al. (1979) "Electrophoretic Transfer of Proteins from Polyacrylamide Gels to Nitrocellulose Sheets: Procedure and Some Applications," 76 *Proc. Natl. Acad. Sci. USA* 4350-4354.
Susskind et al. (1982) "Bacteriophage P22 Antirepressor and Its Control," In R. W. Hendrix et al. (eds.), Lambda II, Cold Spring Harbor Laboratory Press, Cold Spring Harbor, NY, pp. 347-363.
Beck et al. (1983) "Vinca Alkaloid-Resistant Phenotype in Cultured Human Leukemic Lymphoblasts," 67 *Cancer Treat.* 875-882.
Flynn et al. (1983) "The Amino Acid Sequence of an Atrial Peptide with Potent Diuretic and Natriuretic Properties," 117 *Biochem. Biophys. Res. Commun.* 859-865.
Porpaczy et al. (1983) "Association Between the α-Ketoglutarate Dehydrogenase Complex and Succinate Thiokinase," 749 *Biochem. Biophysica. Acta.* 172-179.
Campbell (1984), *Monoclonal Antibody Technology: Laboratory Techniques in Biochemistry and Molecular Biology*, Elsevier Science Publisher, Amsterdam, The Netherlands.
Gros et al. (1986) "Mammalian Multidrug Resistance Gene: Complete cDNA Sequence Indicates Strong Homology to Bacterial Transport Proteins," 47 *Cell* 371-380.
Roninson et al. (1986) "Isolation of Human mdr DNA Sequences Amplified in Multidrug-resistant KB Carcinoma Cells," 83 *Proc. Natl. Acad. Sci. USA* 4538-4542.
Safa et al. (1986) "Vinblastine Photoaffinity Labeling of a High Molecular Weight Surface Membrane Glycoprotein Specific for Multidrug-Resistant Cells," 261 *J. Biol. Chem.* 6137-6140.
Morvan et al. (1987), "α-DNA I. Synthesis, characterization by high field $^1$H-NMR, and Base-pairing properties of the unnatural hexadeoxyribonucleotide α-[d(CpCpTpTpCpC)] with its complement β-[d(GpGpApApGpG)]," 14 *Nucl. Acids Res.* 5019-5035.

Van der Bliek et al. (1987) "The Human *mdr3* Gene Encodes a Novel P-Glycoprotein Homologue and Gives Rise to Alternatively Spliced mRNAs in Liver," 6 *The EMBO J.* 3325-3331.
Haga et al. (1988) "GTP-binding-protein-coupled Receptor Kinase 2 (GRK2) Binds and Phosphorylates Tubulin," 255 *Eur. J. Biochem.* 363-368.
Harlow et al. (1988), *Antibody—A Laboratory Manual*, Cold Spring Harbor Laboratories, Cold Spring Harbor, NY.
Landschulz et al. (1988) "The Leucine Zipper: A Hypothetical Structure Common to a New Class of DNA Binding Proteins," 240 *Science* 1759-1764.
Martini et al. (1988) "Inherited Demyelinating neurpathies: From Gene to Disease," 11 *Curr. Opin. Neurol.* 545-556.
Prelich et al. (1989) "Functional Identity of Proliferating Cell Nuclear Antigen and a DNA Polymerase-δ Auxiliary Protein," 326 *Nature* 517-520.
Sambrook et al. (1989), *Molecular Cloning—A Laboratory Manual*, Cold Spring Harbor Laboratories, Cold Spring Harbor, NY.
Boscoboinik et al. (1990) "Dimerization of the P-glycoprotein in Membranes," 1027 *Biochimica et Biophysica Acta* 225-228.
Chambers et al. (1990) "Correlation of Protein Kinase G Translocation, P-glycoprotein Phosphorylation and Reduced Drug Accumulation in Multidrug Resistant Human KB Cells," 169 *Biochem. Biophys. Res. Commun.* 253-259.
Devault et al. (1990) "Two Members of the Mouse *mdr* Gene Family Confer Multidrug Resistance with Overlapping but Distinct Drug Specificities," 10 *Mol. Cell. Biol.* 1652-1663.
Ford et al. (1990) "Pharmacology of Drugs that Alter Multidrug Resistance in Cancer," 42 *Pharmacol. Rev.* 155-199.
Georges et al. (1990) "Multidrug Resistance and Chemosensitization: Therapeutic Implications for Cancer Chemotherapy," 21 *Advances in Pharmacol.* 185-220.
Grogan et al. (1990) "Optimization of Immunocytochemical P-Glycoprotein Assessment in Multidrug-Resistant Plasma Cell Myeoloma Using Three antibodies," 63 *Lab. Invest.* 815-824.
Herweijer et al. (1990) "Expression of *mdr 1* and *mdr3* Multidrug-resistance Genes in Human Acute and Chronic Leukeimas and Association With Stimulation of Drug Accumulation by Cyclosporine," 82 *J. Nat. Cancer Inst.* 1133-1140.
Ro et al. (1990) "Immunohistochemical Analysis of P-Glycoprotein Expression Correlated with Chemotherapy Resistance in Locally Advanced Breast Cancer," 21 *Human Pathol.* 787-791.
Weinstein et al. (1990) "P-Glycoproteins in Pathology: The Multidrug Resistance Gene Family in Humans," 21 *Human Pathol.* 34-48.
Chan et al. (1991) "P-glycoprotein Expression as a Predictor of the Outcome of Therapy for Neuroblastoma," 325 *N. E. Journ. Med.* 1608-1614.
Georges et al. (1991) "Modulation of ATP and Drug Binding by Monoclonal Antibodies Against P-Glycoprotein," 148 *J. Cell. Physiol.* 479-484.
Schinkel et al. (1991) "Characterization of the Human *MDR3* P-Glycoprotein and Its Recognition by P-Glycoprotein-specific Monoclonal Antibodies," 51 *Cancer Res.* 2628-2635.
Verrelle et al. (1991) "Clinical Relevance of Immunohistochemical Detection of Multidrug Resistance P-Glycoprotein in Breast Carcinoma," 83 *J. Nat. Cancer Inst.* 111-116.
Bates et al. (1992) "Modulation of P-Glycoprotein Phosphorylation and Drug Transport by Sodium Butyrate," 31 *Biochem.* 6366-6372.
Gill et al. (1992) "Separation of Drug Transport and Chloride Channel Functions of the Human Multidrug Resistance P-glycoprotein," 71 *Cell* 23-32.
Higgins (1992) "ABC Transporters: From Microorganisms to Man," 8 *Ann. Rev. of Cell Biol.* 67-113.
Naito et al. (1992) "Functionally Active Homodimer of P-Glycoprotein in Multidrug-Resistant Tumor Cells," 185 *Biochem. Biophys. Res. Commun.* 284-290.
Pawson et al. (1992) "SH2 and SH3 Domains: From Structure to Function," 71 *Cell* 359-362.
Valverde et al. (1992) "Volume-regulated Chloride Channels Associated with the Human Multidrug-resistance P-glycoprotein," 355 *Nature* 830-833.

Adorini et al. (1993) "Selective Inhibition of T cell Responses by Protein and Peptide-based Immunotherapy," 8 *Clin. Exp. Rheumatol.* S41-44.

Bates et al. (1993) "Differential Modulation of P-Glycoprotein Transport by Protein Kinase Inhibition," 37 *Biochemistry* 9156-9264.

Chambers et al. (1993) "Identification of Specific Sites in Human P-glycoprotein Phosphorylated by Protein Kinase C*," 268 *J. Biol. Chem.* 4592-4595.

Felder et al. (1993) "SH2 Domains Exhibit High-Affinity Binding to Tyrosine-Phosphorylated Peptides yet Also Exhibit Rapid Dissociation and Exchange," 13 *Mol. Cell. Biol.* 1449-1455.

Futscher et al. (1993) "Quantitive Polymerase Chain Reaction Analysis of mdr1 mRNA in Multiple Myeloma Cell Lines and Clinical Specimens," 213 *Anal. Biochem.* 414-421.

Gottesman et al. (1993) "Biochemistry of Multidrug Resistance Mediated by the Multidrug Transporter," 62 *Ann. Rev. Biochem.* 385-427.

Li et al. (1993) "Guanine-nucleotide-releasing Factor hSos1 Binds to Grb2 and Links Receptor Tyrosine Kinases to Ras Signalling," 363 *Nature* 85-88.

List et al. (1993) "Phase I/II Trial of Cyclosporine as a Chemotherapy-Resistance Modifier in Acute Leukemia," 11 *J. Clin. Oncol.* 1652-1660.

Safa et al. (1993) "Photoaffinity Labeling of P-Glycoprotein in Multidrug-Resistant Cells," 11 *Cancer Invest.* 46-56.

Smit et al. (1993) "Homozygous Disruption of the Murine *mdr2* P-Glycoprotein Gene Leads to a Complete Absence of Phospholipid from Bile and to Liver Disease," 75 *Cell* 451-462.

Ahmad et al. (1994) "Modulation of P-Glycoprotein by Protein Kinase Cα in a Baculovirus Expression System," 33 *Biochem.* 10313-10318.

Buschman et al. (1994) "The Inability of the Mouse *mdr2* Gene to Confer Multidrug Resistance Is Linked to Reduced Drug Binding to the Protein," 54 *Cancer Res.* 4892-4898.

Chambers et al. (1994) "Phosphorylation by Protein Kinase C and Cyclic AMP-dependent Protein Kinase of Synthetic Peptides from the Liver Region of Human P-glycoprotein," 299 *Bichem. J.* 309-315.

Childs et al. (1994) "The MDR Superfamily of Genes and Its Biological Implications," *Important Adv. Oncol.* pp. 21-36.

Cornelissen et al. (1994) "MDR-1 Expression and Response to Vincristine, Doxorubicin, and Dexamethasone Chemotherapy in Multiple Myeloma Refractory to Alkylating Agents," 12 *J. Clin. Oncol.* 115-119.

Fields et al. (1994) "The Two-hybrid System: An Assay for Protein-protein Interactions," 10 *Trend. Genet.* 286-292.

Nare et al. (1994) "Benzimidazoles, Potent Anti-Mitotic Drugs: Substrates for the P-Glycoprotein Transporter in Multidrug-Resistant Cells," 48 *Biochem. Pharmacol.* 2215-2222.

Nooter et al. (1994) "Clinical Relevance of P-Glycoprotein Expression in Haematological Malignancies," 18 *Leukemia Res.* 233-243.

Ruetz et al. (1994) "Functional Expression of P-glycoproteins in Secretory Vesicles," 269 *J. Biol. Chem.* 12277-12284.

Schinkel et al. (1994) "Disruption of the Mouse *mdr1a* P-Glicoprotein Gene Leads to a Deficiency in the Blood-Brain Barrier and to Increased Sensitivity to Drugs," 77 *Cell* 491-502.

Sonneveld et al. (1994) "Clinical Modulation of Multidrug Resistance in Multiple Myeolma: Effect of Cyclosporine on Resistant Tumor Cells," 12 *J. Clin. Oncol.* 1584-1591.

Bates et al. (1995) "A Pilot Study of Amiodarone with Infusional Doxorubicin or Vinblastine in Refractory breast Cancer," 35 *Cancer Chemother. & Pharmacol.* 457-463.

Chan et al. (1995) "Multidrug Resistance in Pediatric Malignanacies," 9 *Hematol.-Oncol. Clin. of N. Amer.l* 275-318.

Dalton et al. (1995) "A Phase III Randomized Study of Oral Verapamil as a Chemosensitizer to Reverse Drug Resistance in Patients with Refractory Myeloma," 75 *Cancer* 815-820.

Goldstein (1995) "Clinical Reversal of Drug Resistance," 19 *Curr. Probl. Cancer* 65-124.

Gottesman et al. (1995) "Genetic Analysis of the Multidrug Transporter," 29 *Annu. Rev. Genet.* 607-649.

Hardy et al. (1995) "Protein Kinase C-mediated Phosphorylation of the Human Multidrug Resistance P-glycoprotein Regulates Cell Volume-activated Chloride Channels," 14 *The EMBO Journal* 68-75.

Heldin (1995) "Dimerization of Cell Surface Receptors in Signal Transduction," 80 *Cell* 213-223.

Hoogenboom et al. (1995) "Antibody Phage Display Technology and Its Application," 4 *Immunotechnology* 1-20.

Jacobson et al. (1995) "Revisiting the Fluid Mosaic Model of Membranes," 268 *Science* 1441-1442.

Loo et al. (1995) "Membrane Topology of a Cysteine-less Mutant of Human P-glycoprotein," 270 *J. Biol. Chem.* 843-848.

Perrot-Applanat et al. (1995) "The 59 kDa FK506-binding Protein, a 90 kDa Heat Shock Protein Binding Immunophilin (FKBP59-HBI), Is Associated with the Nucleus, the Cytoskeleton and Mitotic Apparatus," 108 *J. Cell. Sci.* 2037-2051.

Phizicky et al. (1995) "Protein-protein Interactions: Methods for Detection and Analysis," 59 *Microbiol. Rev.* 94-123.

Sako et al. (1995) "Barriers for Lateral Diffusion of Transferrin Receptor in the Plasma Membrane as Characterized by Receptor Dragging by Laser Tweezers: Fence versus Tether," 129 *J. Cell. Biol.* 1559-1574.

Stanfield et al. (1995) "Protein-peptide Interactions," 5 *Curr. Opin. Struct. Biol.* 103-113.

Wilson et al. (1995) "Coupled Translation/Prenylation of Rab Proteins *in* Vitro," 250 *Methods. Enzymol.* 79-91.

Cole et al. (1996) "Multidrug Resistance Associated with Overexpression of MRP," 87 *Cancer Treatment & Res.* 39-62.

Germann et al. (1996) "Characterization of Phosphorylation-defective Mutants of Human P-glycoprotein Expressed in Mammalian Cells," 271 *J. Biol. Chem.* 1708-1716.

Gupta (1996) "P-glycoprotein Expression in Normal Hematopoietic Progenitors and Cells of the Immune System" in *Multidrug Resistance in Cancer Cells: Molecular, Biochemical, Physiological and Biological Aspects*, Editors Gupta, S. and Tsuruo, T., John Wiley & Sons, pp. 293-302.

Mailliard et al. (1996) "Calcium-dependent Binding of S100C to the N-terminal Domain of Annexin I," 271 *J. Biol. Chem.* 719-725.

Molina et al. (1996) "Improved Performance of Spot Multiple Peptide Synthesis," 9 *Pept. Res.* 151-155.

O'Brien et al. (1996) "P-glycoprotein Expression in Normal Human Tissues," in *Multidrug Resistance in Cancer Cells: Molecular, Biochemical, Physiological and Biological Aspects*, Editors Gupta, S. and Tsuruo, T., John Wiley & Sons, pp. 285-292.

Reed et al. (1996) "BCL-2 Family Proteins: Regulators of Cell Death Involved in the Pathogenesis of Cancer and Resistance to Therapy," 60 *J. Cell. Biochem.* 23-32.

Tousson et al. (1996) "Apical Recruitment of CFTR in T-84 Cells Is Dependent on cAMP and Microtubules but not $Ca^{2+}$ or Microfilaments," *J. Cell. Sci.* 1325-1334.

Wigler (1996) 28 "Cellular Drug Efflux and Reversal Therapy of Cancer," *J. Bioenerg. Biomembr.* 279-284.

Chen et al. (1997) "Recognition of Neutral Species with Synthetic Receptors," 1 *Curr. Opin. Chem. Biol.* 458-466.

Ehrmann et al. (1997) "Prognostic Factors in Astrocytomas: Relationship pf p53, MDM-2. BCL-2 and PCNA Immunohistochemical Expression to Tumor Grade and Overall Patient survival," 44 *Neoplasma* 299-304.

Glavy et al. (1997) "Identification of the *in Vivo* Phosphorylation Sites for Acidic-directed Kinases in Murine *mdr*1b P-glycoprotein," 272 *J. Biol. Chem.* 5909-5914.

Kast et al. (1997) "Topology Mapping of the Amino-terminal Half of Multidrug Resistance-associated Protein by Epitope Insertion and Immunofluorescence," 272 *J. Biol. Chem.* 26479-26487.

Kuriyan et al. (1997) "Modular Peptide Recognition Domains in Eukaryotic Signalling," 26 *Ann. Rev. Biophys. Biomol. Struct.* 259-288.

Ling (1997) "Multidrug Resistance: Molecular Mechanisms and Clinical Relevance," 40 *Cancer Chemother. Pharmacol.* Suppl. S3-8.

McCoy et al. (1997) "Hydrophobic Side-chain Size Is A Determinant of the Three-Dimensional Structure of the p53 Oligomerization Domain," 16 *EMBO J.* 6230-6236.

Ravindra (1997) "Is Signal Transduction Modulated by an Interaction Between Heterotrimeric G-Proteins and Tubulin?" 7 *Endocrine* 127-143.

Rosenberg et al. (1997) "Structure of the Multidrug Resistance P-glycoprotein to 2.5 nm Resolution Determined by Electron Microscopy and Image Analysis," 272 *J. Biol. Chem.* 10685-10694.

Alba et al. (1998) "Rapid Fluorescent Monitoring of Total Protein Patterns on Sodium Dodecyl Sulfate-polyacrylamide gels and Western Blots Before immunodetection and Sequencing," 19 *Electrophoresis* 2407-2411.

Giustetto et al. (1998) "Localization of the Clustering Protein Gephyrin at GABAergic Synapses in the Main Olfactory Bulb of the Rat," 395 *J. Comp. Neurol.* 231-244.

Klemm et al. (1998) "Dimerization as a Regulatory Mechanism in Signal Transduction," 16 *Ann. Rev. Immunol.* 569-592.

Lee et al. (1998) "Increased P-glycoprotein Messenger RNA Stability in Rat Liver Tumors in Vivo," 177 *J. Cell. Physiol.* 1-12.

Miller et al. (1998) "Oligonucleotide Inhibitors of Gene Expression in Living Cells: New Opportunities in Drug Design," 23 *Ann. Reports Med. Chem.* 295-304.

Ramsay et al. (1998) "DNA Chips: State-of-the Art," 16(1) *Natl. Biotechnol.* 40-44.

Schena et al. (1998) "Microarrays: Biotechnology's Discovery Platform for Functional Genomics," 16(7) *Trends Biotechnol.* 301-306.

Stefanou et al. (1998) "p53 /MDM Immunohistochemical Expression Correlated with Proliferative Activity in Different Subtypes of Human Sarcomas: A Ten-Year Follow-up Study," 18 *Anticancer* 4673-4681.

Stevenson et al. (1998) "Coupling Capillary High-Performance Liquid Chromatography to Matrix-Assisted Laser Desorption/Ionization Mass Spectrometry and N-Terminal Sequencing of Peptides via Automated Microblotting onto Membrane Substrates," 262 *Anal. Biochem.* 99-109.

Brown et al. (1999) "Exploring the New World of the Genome with DNA Microarrays," 21(1) *Nat. Genet.* 33-37.

Cheung et al. (1999) "Making and Reading Microarrays," 21(1) *Nat. Genet.* 15-19.

Duggan et al. (1999) "Expression Profiling Using cDNA Microarrays," 21(1) *Natl. Genet.* 10-14.

Jolliet-Riant et al. (1999) "Drug Transfer Across the Blood-Brain Barrier and Improvement of Brain Delivery," 13 *Fundam. Clin. Pharmacol.* 16-26.

Debouck et al. (1999) "DNA Microarrays in Drug Discovery and Development," 21 *Nature Genetics Supplement*, 48-50.

Fine et al (1988) "Phorbol Esters Induce Multidrug Resistance in Human Breast Cancer Cells," 85 *Proc. Natl. Acad. Sci.* 582-586.

O'Brien et al. (1996) "P-glycoprotein Expression in Normal Human Tissues," in S. Gupta and T. Tsurucy (eds.), John Wiley & Sons Ltd., *Multidrug Resistance in Cancer Cells*, 285-291.

Watanabe et al. (1995), "Comparative Study on Reversal Efficacy of SDZ PSC 833, Cyclosporin A and Verapamil on Multidrug Resistance In Vitro and In Vivo," 34 *Acta Oncologica*, 235-241.

Robert F. Ozols, Editor-in-Chief, "Clinical Reversal of Drug Resistance," in *Current Problems In Cancer*, vol. XIX, No. 2, Mar./Apr. 1995, 67-124.

Rivero-Lezcano, et al., "Specificity of Protein Interactions with Highly Related SRC Homology (SH) Domains of FGR and FYN Protein-Tyrosine Kinases", FEBS Letters, 338:183-186 (1994).

Kitay, et al., "Protein-Protein Interactions Between Epstein-Barr Virus Nuclear Antigen-LP and Cellular Gene Products: Binding of 70-Kilodalton Heat Shock Proteins", Virology, 220:91-96 (1996).

* cited by examiner

Alignment Of Amino Acid Sequences Of Human P-gp3 And P-gp1
Linker Domains

```
618 LMKKEGVYFKLVNMQTSGSQIQSEEF--ELNDEKAATRMAPNGWKSRLFR-HSTQKNLKNSQM 677   P-gp3
    LMK++G+YFKLV MQT+G++++ E   E  E A M+ N  +S L R  ST++++
615 LMKEKGIYFKLVTMQTAGNEVELENAADESKSEIDALEMSSNDSRSSLIRKRSTRRSVRGSQA 677   P-gp1

678 CQKSLDVETDGLEANVPPVSFLKVLKLNKTEWP 710   P-gp3 (SEQ. ID NO: 14)
    + L + + L+ ++PPVSF +++KLN TEWP
678 QDRKLSTK-EALDESIPPVSFWRIMKLNLTEWP 709   P-gp1 (SEQ. ID NO: 15)
```

FIG. 10

HELICAL WHEEL PRESENTATION
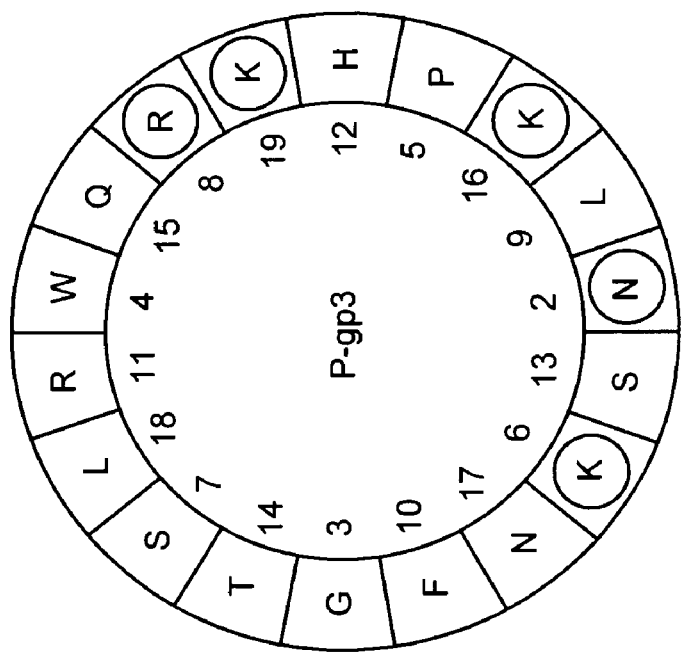
NGWKSRLFRHSTQKNLK (SEQ. ID NO: 13)
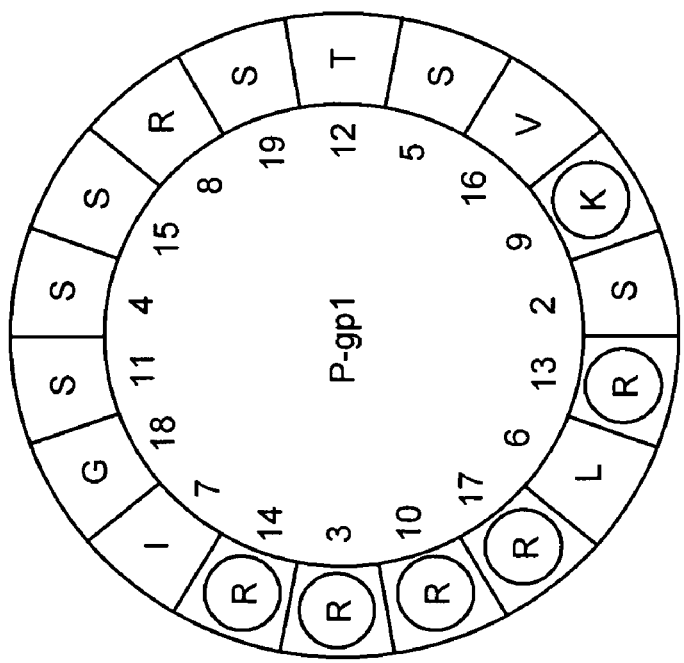
SRSSLIRKRSTRRSVRGS (SEQ. ID NO: 12)
FIG. 15

PROTEIN-PROTEIN INTERACTIONS AND METHODS FOR IDENTIFYING INTERACTING PROTEINS AND THE AMINO ACID SEQUENCE AT THE SITE OF INTERACTION

CROSS REFERENCE TO RELATED APPLICATIONS

This application is a continuation of PCT Application No. PCT/CA00/0587, filed May 12, 2000, which claims priority from U.S. Provisional Application No. 60/134,259, filed May 14, 1999, the entire contents of both of which are hereby incorporated by reference.

FIELD OF THE INVENTION

The present invention relates to proteomics. More specifically, the invention relates to protein-protein interactions and methods for identifying interacting proteins and the amino acid sequence at the site of interaction.

BACKGROUND OF THE INVENTION

Specific protein-protein interactions are critical events in biological processes. Protein-protein interactions govern biological processes that handle cellular information flow and control cellular decisions (e.g., signal transduction, cell cycle regulation and assembly of cellular structures). The entire network of interactions between cellular proteins is a biological chart of functional events that regulate the internal working of living organisms and their responses to external signals. A necessary step for the completion of this biological interaction chart is the knowledge of all the gene sequences in a given living organism. The entire DNA sequence of the *Homo sapiens* genome will be completed at the latest by the year 2003 (112). Unfortunately, the sequence of a gene does not reveal its biological function nor its position in the biological chart. Given the expected number of proteins in the human genome (80,000 to 120,000), the mapping of the biological chart of protein-protein interactions will be an enormous but a rewarding task.

During the past few decades, several techniques have been developed to determine the interactions between proteins (for review, see (82)). These techniques include, i) physical methods to select and detect interacting proteins (e.g., protein affinity chromatography, co-immunoprecipitation, crosslinking, and affinity blotting), ii) Library based methods (e.g., Phage display and two-hybrid systems); and iii) genetic methods (e.g., overproduction phenotype, synthetic lethal effects and unlinked noncomplementation). Of the above mentioned methods for detecting protein-protein interactions, the two-hybrid systems are most popular and are most extensively used. In the classical two-hybrid system (30), transcription of reporter genes depends on an interaction between a DNA-bound "bait" protein and an activation-domain containing "prey" protein. The two hybrid systems unfortunately may suffer from a number of disadvantages. For example, the interaction of proteins is monitored in the nuclear milieu rather than the cytoplasm where most proteins are found and it does not allow the simultaneous identification of the precise amino acid sequences between two interacting proteins and cannot be easily applied to different cell types or tissues whereby different interacting proteins may be expressed.

It has been previously demonstrated that small synthetic peptides can bind to proteins (1, 18, 55, 102). Nevertheless, the use of synthetic peptides in a systematic approach to identify interacting protein domains and sequences has not been proposed or provided. Certain signature domains have been shown to bind with high affinity to specific peptide sequences (e.g., the Src homology-2 or SH2 domain of Src-family kinases bind tightly to a phosphorylated tyrosine (Y*-EEI) sequence (SEQ ID NO: 9) found in epidermal growth factor receptor and the focal adhesion kinase) (61).

There thus remains a need to provide a method which enables identification of i) the exact amino acid sequences of at least one binding partner between interacting proteins; ii) numerous, possibly all interacting proteins in different cells or tissues; and iii) the specific domains (or sequences) between two interacting proteins as targets for isolation of lead drugs. In addition, there remains a need to provide methods and assays which enable the identification of the precise amino acid sequence of interacting domains of proteins which is significantly faster than conventional methods (e.g., days instead of months).

The present invention seeks to meet these and other needs.

The present description refers to a number of documents, the content of which is herein incorporated by reference, in their entirety.

SUMMARY OF THE INVENTION

The present invention seeks to overcome the drawbacks of the prior art. More specifically, the invention concerns an approach to identify protein-protein interaction domains which differ from the prior art. Moreover, one approach of the present invention is based on an understanding of the principle that governs protein-protein interactions. Such understanding therefore, allows the use of several methods. Such a method is exemplified in detail below to identify: i) at least one of the exact amino acid sequences between interacting proteins; ii) a number of, possibly all, interacting proteins in different cells or tissues; and iii) the specific domains (or sequences) between two interacting proteins as targets for isolation of lead drugs. Preferably, the method and assay of the present invention enable a determination of i), ii) and iii). Moreover, unlike the approaches of the prior art, the method described herein allows for the identification of interacting proteins and the precise amino acid sequences of interactions in several days as opposed to several months.

The ability to select proteins (or other molecules) that block interactions between a gene product and some partners but not others, should allow sophisticated modulation of cellular signaling or cell metabolism in human cells and other currently interactable systems. Indeed, the identification of proteins that interact with a therapeutically important protein and the identification of the sites of interaction may be more relevant to drug development than other genetic approaches such as "knock-outs" (71). The latter addresses the phenotypic consequences of disrupting all of the interactions in which a given protein is involved as opposed to inhibiting the interaction of one protein (at worse of a few proteins as opposed to all) in a multimeric complex.

The present invention further relates to a novel approach in drug discovery. A major obstacle in drug development for the treatment of diseases has been the identification of target proteins and their functional sites. In fact, most research and development (R&D) projects in pharmaceutical companies take several years to identify a valid target protein. The selection of drugs that bind to and inhibit the functions of these proteins takes several years and is generally non-specific and random. Furthermore, drugs identified by current approaches often target the active sites in proteins. Such drugs thus often lead to major side-effects. Therefore, it is not surprising that many R&D projects never lead to the development of specific drugs even after three to five years of intensive research efforts. The methods and assays to identify protein-protein interactions of the present invention may address three important steps in the development of drugs:

1) the identification of the amino acid sequences of all interacting domains in target proteins;

2) the identification of a set of interacting proteins (preferably all interacting proteins) for drug development; and 3) screening for specific drugs against each of the interacting domains in a target protein.

P-glycoprotein (P-gp) has been shown to cause multidrug resistance in tumor cell lines selected with lipophilic anti-cancer drugs. Analysis of P-gp amino acid sequence has lead to a proposed model of a duplicated molecule with two hydrophobic and hydrophilic domains linked by a highly charged region of about 90 amino acids, the linker domain. Although similarly charged domains are found in other members of the P-gp superfamily, the function(s) of this domain are not known. Herein, it is demonstrated using the method of the present invention that this domain binds to other cellular proteins. Using overlapping hexapeptides that span the entire amino acid sequences of the linker domains of human P-glycoprotein gene 1 and 3 (HP-gp1 and HP-gp3), a direct and specific binding between HP-gp1 and 3 linker domains and intracellular proteins is shown herein. Three different stretches ($^{617}$EKGIYFKLVTM$^{627}$ (SEQ ID NO: 1), $^{658}$SRSSLIRKRSTRRSVRGSQA$^{677}$ (SEQ ID NO: 2) and $^{694}$PVSFWRIMKLNLT$^{706}$ (SEQ ID NO: 3) for HP-gp1 and $^{618}$LMKKEGVYFKLVNM$^{631}$ (SEQ ID NO: 4), $^{648}$KAATRMAPNGWKSRLFRHSTQKNLKNS$^{674}$ (SEQ ID NO: 5) and $^{695}$PVSFLKVLKLNKT$^{707}$ (SEQ ID NO: 6) for HP-gp3) in linker domains specifically bound to proteins with apparent molecular masses of ~80 kDa, 57 kDa and 30 kDa. Interestingly, only the 57 kDa protein was bound, to varying degrees, to the three different sequences in the linker domain. Moreover, the binding between the overlapping peptides encoding the linker sequence and the 57 kDa protein were resistant to the zwitterionic detergent, CHAPS, but were sensitive to SDS. Purification and partial N-terminal amino acid sequencing of the 57 kDa protein showed that it encodes the N-terminal amino acids of alpha and beta-tubulins. Further, Western blot analysis using monoclonal antibodies that binds to α- and β-tubulins confirmed the identity of the 57 kDa protein. Taken together, this is the first example showing protein interactions with the P-gp linker domain. This may of course be important to the overall function of P-gp. More importantly, the results in this study demonstrate the novel concept whereby the interactions between two proteins are mediated by strings of few amino acids with high and repulsive binding energies.

In accordance with one embodiment of the present invention, there is provided a method of identifying a high affinity interacting domain in a chosen protein, domain thereof, or part thereof, and the amino acid sequence thereof comprising: a) providing a set of overlapping peptides spanning a complete sequence of the chosen protein, domain thereof, or part thereof, covalently bound to a support; b) providing a mixture of proteins and/or a mixture of peptides; c) incubating the set of overlapping peptides of a), with the mixture of b), under conditions enabling the binding between a high affinity interacting domain in a peptide of the set and one or more protein or peptide of b) to occur; d) washing off any protein-protein interaction which is not a high affinity interaction of c); and e) identifying which peptide of a) interacts with high affinity to a protein or peptide of b), thereby identifying the peptide of e) and the sequence thereof as a high affinity interacting domain.

In accordance with another embodiment of the present invention, there is provided a method of identifying an agent which modulates an interaction between high affinity interacting domains between a set of overlapping peptides spanning a complete sequence of a chosen protein, domain thereof or part thereof, covalently bound to a support and a mixture of proteins and/or a mixture of peptides comprising: a) incubating the set of overlapping peptides, with the mixture in the presence of at least one agent, under conditions enabling the binding between a high affinity interacting domain in a peptide of the set and one or more protein or peptide of the mixture to occur; b) washing off any protein-protein interaction which is not a high affinity interaction of b); and c) identifying which peptide of a) interacts with high affinity to a protein or peptide of the mixture in a presence of the agent as compared to in an absence thereof; thereby identifying the agent as a modulator of the high affinity interaction when the interaction in the presence of the agent is measurably different from in the absence thereof.

In accordance with yet another embodiment of the present invention, there is provided agents identified as modulators of the high affinity protein interactions of the present invention.

For the purpose of the present invention, the following abbreviations and terms are defined below.

DEFINITIONS

The terminology "overlapping peptides spanning a peptide sequence" (e.g., a domain, a full length protein sequence or a part thereof) or the like refers to peptides of a chosen size, based on the sequence of the protein (or part thereof). Preferably, these peptides are synthetic peptides.

As explained hereinbelow, the size of the overlapping peptides has a significant impact on the workings of the present invention. For example, peptides of four contiguous amino acids appear to significantly increase the low affinity binding of proteins thereto. Moreover, the use of larger peptides, such as 20 amino acids or higher, would be expected to increase the proportion of repulsive amino acids to high affinity amino acids, thereby masking or totally inhibiting the binding of specific proteins to the peptides. Thus, while the person of ordinary skill would understand that there are trade-offs associated with the choice of small peptides as opposed to larger ones, the preferred size for the overlapping peptides of the present invention is between 5 and 15 amino acids, more preferably between 5 and 12, and especially preferably between 5 and 10 amino acids.

The term "support" in the context of a support to which the overlapping peptides of the present invention are covalently bound, can be chosen from a multitude of supports found in the art. Such supports include CHIPS, plates (e.g. 96-well plates), glass beads and the like. The CHIP technology is well-known in the art (10, 19, 24, 26, 85, 97).

Protein sequences are presented herein using the one letter or three letter amino acid symbols as commonly used in the art and in accordance with the recommendations of the IUPAC-IUB Biochemical Nomenclature Commission.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals (4, 96).

The present description refers mainly to proteins, or recombinant DNA (rDNA) technology terms. Selected examples are provided for clarity and consistency.

As used herein, "nucleic acid molecule", refers to a polymer of nucleotides. Non-limiting examples thereof include DNA (e.g. genomic DNA, cDNA) and RNA molecules (e.g., mRNA). The nucleic acid molecule can be obtained by cloning techniques or synthesized. DNA can be double-stranded or single-stranded (coding strand or non-coding strand [antisense]).

The term "recombinant DNA" as known in the art refers to a DNA molecule resulting from the joining of DNA segments. This is often referred to as genetic engineering.

The term "DNA segment," is used herein, to refer to a DNA molecule comprising a linear stretch or sequence of nucleotides. This sequence when read in accordance with the genetic code, can encode a linear stretch or sequence of amino acids which can be referred to as a polypeptide, protein, protein fragment and the like.

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions.

The nucleic acid (e.g. DNA or RNA) for practicing the present invention may be obtained according to well known methods.

As used herein, the term "physiologically relevant" is meant to describe interactions which can take effect to modulate an activity or level of one or more proteins in their natural setting.

The term "DNA" molecule or sequence (as well as sometimes the term "oligonucleotide") refers to a molecule comprised of the deoxyribonucleotides adenine (A), guanine (G), thymine (T) and/or cytosine (C), in a double-stranded form, and comprises or includes a "regulatory element" according to the present invention, as the term is defined herein. The term "oligonucleotide" or "DNA" can be found in linear DNA molecules or fragments, viruses, plasmids, vectors, chromosomes or synthetically derived DNA. As used herein, particular double-stranded DNA sequences may be described according to the normal convention of giving only the sequence in the 5' to 3' direction.

"Nucleic acid hybridization" refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (4, 96) and are commonly known in the art. In the case of hybridization to a nitrocellulose filter, as for example in the well known Southern blotting procedure, a nitrocellulose filter can be incubated overnight at 65° C. with a labeled probe in a solution containing 50% formamide, high salt (5×SSC or 5×SSPE), 5×Denhardt's solution, 1% SDS, and 100 μg/ml denatured carrier DNA (e.g., salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The selected temperature is based on the melting temperature (Tm) of the DNA hybrid. Of course, RNA-DNA hybrids can also be formed and detected. In such cases, the conditions of hybridization and washing can be adapted according to well-known methods by the person of ordinary skill. Stringent conditions will be preferably used (96).

Probes for nucleic acids can be utilized with naturally occurring sugar-phosphate backbones as well as modified backbones including phosphorothioates, dithionates, alkyl phosphonates and α-nucleotides and the like. Modified sugar-phosphate backbones are generally taught (73, 75). Probes of the invention can be constructed of either ribonucleic acid (RNA) or deoxyribonucleic acid (DNA), and preferably of DNA.

It is an advantage of the present invention that the detection of the interaction between proteins and/or peptides be dependent on a label. Such labels provide sensitivity and often enable automation. In one embodiment of the present invention, automation is performed using CHIP technology. For example, the overlapping peptides spanning a chosen sequence of a protein, are bound to a CHIP which can then be used to automate a test for interaction with proteins or peptides. Of course, it should be understood that the present invention is not strictly dependent on a design and synthesis of the overlapping set of peptides spanning a chosen protein sequence. Indeed, banks of peptides are available, from which this set of overlapping peptides could be constructed.

Protein labelling is well known in the art. Non-limiting examples of labels include $^3$H, $^{14}$C, $^{32}$P, and $^{35}$S. Non-limiting examples of detectable markers include ligands, fluorophores, chemiluminescent agents, enzymes, and antibodies. It will become evident to the person of ordinary skill that the choice of a particular label dictates the manner in which it is bound to the protein.

The identification of the interaction is not specifically dependent on labelling of the proteins, since for example, this interaction could be assessed using proteomic approaches (such as 2-D gels and mass spectrometry) or using a library of antibodies.

As commonly known, radioactive amino acids can be incorporated into peptides or proteins of the invention by several well-known methods. A non-limiting example thereof includes in vitro or in vivo labelling of proteins using $^{35}$SMet.

The term "vector" is commonly known in the art and defines a plasmid DNA, phage DNA, viral DNA and the like, which can serve as a DNA vehicle into which DNA of the present invention can be cloned. Numerous types of vectors exist and are well known in the art.

The term "expression" defines the process by which a gene is transcribed into mRNA (transcription), the mRNA then being translated (translation) into one polypeptide (or protein) or more.

The terminology "expression vector" defines a vector or vehicle as described above, but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

Operably linked sequences may also include two segments that are transcribed into the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

Expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

Prokaryotic expression is useful for the preparation of large quantities of the protein encoded by the DNA sequence of interest. This protein can be purified according to standard protocols that take advantage of the intrinsic properties thereof, such as size and charge (e.g., SDS gel electrophoresis, gel filtration, centrifugation, ion exchange chromatography, etc.). In addition, the protein of interest can be purified via affinity chromatography using polyclonal or monoclonal antibodies. The purified protein can be used for therapeutic applications.

The DNA construct can be a vector comprising a promoter that is operably linked to an oligonucleotide sequence of the present invention, which in turn is operably linked to a heterologous gene, such as the gene for the luciferase reporter molecule. "Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boxes and "CCAT" boxes. Prokaryotic promoters contain Shine-Dalgarno sequences in addition to the −10 and −35 consensus sequences.

As used herein, the designation "functional derivative" denotes, in the context of a functional derivative of a sequence, whether a nucleic acid or amino acid sequence, a molecule that retains a biological activity (either function or structural) that is substantially similar to that of the original sequence. This functional derivative or equivalent may be a natural derivative or may be prepared synthetically. Such derivatives include amino acid sequences having substitutions, deletions, or additions of one or more amino acids, provided that the biological activity of the protein is conserved. The same applies to derivatives of nucleic acid sequences which can have substitutions, deletions, or additions of one or more nucleotides, provided that the biological activity of the sequence is generally maintained. When relating to a protein sequence, the substituting amino acid has chemico-physical properties, which are similar to that of the substituted amino acid. The similar chemico-physical properties include, similarities in charge, bulkiness, hydrophobicity, hydrophilicity and the like. The term "functional derivatives" is intended to include fragments, segments, variants, analogs or chemical derivatives of the subject matter of the present invention.

As well-known in the art, a "conservative mutation or substitution" of an amino acid refers to mutation or substitution which maintains: 1) the structure of the backbone of the polypeptide (e.g. a beta sheet or alpha-helical structure); 2) the charge or hydrophobicity of the amino acid; or 3) the bulkiness of the side chain. More specifically, the well-known terminologies "hydrophilic residues" relate to serine or threonine. "Hydrophobic residues" refer to leucine, isoleucine, phenylalanine, valine or alanine. "Positively charged residues" relate to lysine, arginine or histidine. "Negatively charged residues" refer to aspartic acid or glutamic acid. Residues having "bulky side chains" refer to phenylalanine, tryptophan or tyrosine.

Peptides, protein fragments, and the like in accordance with the present invention can be modified in accordance with well-known methods dependently or independently of the sequence thereof. For example, peptides can be derived from the wild-type sequence exemplified herein in the figures using conservative amino acid substitutions at 1, 2, 3 or more positions. The terminology "conservative amino acid substitutions" is well known in the art, which relates to substitution of a particular amino acid by one having a similar characteristic (e.g. aspartic acid for glutamic acid, or isoleucine for leucine). Of course, non-conservative amino acid substitutions can also be carried out, as well as other types of modifications such as deletions or insertions, provided that these modifications modify the peptide, in a suitable way (e.g. without affecting the biological activity of the peptide if this is what is intended by the modification). A list of exemplary conservative amino acid substitutions is given hereinbelow.

TABLE 2

CONSERVATIVE AMINO ACID REPLACEMENTS

| For Amino Acid | Code | Replace With |
|---|---|---|
| Alanine | A | D-Ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4, or 5-phenylproline, Bpa, D-Bpa |
| Proline | P | D-Pro, L-I-thioazolidine-4-carboxylic acid, D-or L-1-oxazolidine-4-carboxylic acid (Kauer, U.S. Pat. No. (4,511,390) |
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

As can be seen in this table, some of these modifications can be used to render the peptide more resistant to proteolysis. Of course, modifications of the peptides can also be effected without affecting the primary sequence thereof using an enzymatic or chemical treatment well known in the art.

The term "variant" refers herein to a protein or nucleic acid molecule, which is substantially similar in structure and biological activity to the protein or nucleic acid of the present invention.

The functional derivatives of the present invention can be synthesized chemically or produced through recombinant DNA technology, using methods well known in the art. In one particular embodiment of the present invention, a variant according to the present invention can be identified using a method of the present invention. It can also be designed to formally test for the conservation of particular amino acids (e.g. by synthesizing a variant or mutant peptide). These variants can also be tested as part of the full-length sequence of the protein in order to validate the interaction. Of course, the skilled artisan will understand that having identified a region of a chosen protein as a region which is involved in high affinity protein interaction(s) enables an in vitro mutagenesis (or a testing of related peptide sequences) of this region to identify and dissect the structure/function relation of this region. Such methods are well known in the art. When the interaction domains of two proteins having been identified, it is thus possible for the skilled artisan to identify and/or design variants having a modified affinity for an interacting protein. Of course, when both interacting sequences are known, very powerful questions can be asked to dissect the structure-function relationship, which governs the high affinity interaction between same.

As used herein, "chemical derivatives" is meant to cover additional chemical moieties not normally part of the subject matter of the invention. Such moieties could affect the physico-chemical characteristic of the derivative (e.g. solubility, absorption, half life and the like, decrease of toxicity). Such moieties are exemplified in Remington's Pharmaceutical Sciences (88). Methods of coupling these chemical-physical moieties to a polypeptide are well known in the art.

The term "allele" defines an alternative form of a gene, which occupies a given locus on a chromosome.

As commonly known, a "mutation" is a detectable change in the genetic material, which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. The result of a mutation of a nucleic acid molecule is a mutant nucleic acid molecule. A mutant polypeptide can be encoded from this mutant nucleic acid molecule.

As used herein, the term "purified" refers to a molecule having been separated from a cellular component. Thus, for example, a "purified protein" has been purified to a level not found in nature. A "substantially pure" molecule is a molecule that is lacking in most other cellular components.

As used herein, the terms "molecule", "compound" or "ligand" are used interchangeably and broadly to refer to natural, synthetic or semi-synthetic molecules or compounds. The term "molecule" therefore denotes for example chemicals, macromolecules, cell or tissue extracts (from plants or animals) and the like. Non-limiting examples of molecules include nucleic acid molecules, peptides, antibodies, carbohydrates and pharmaceutical agents. The agents can be selected and screened by a variety of means including random screening, rational selection and by rational design using for example protein or ligand modelling methods such as computer modelling, combinatorial library screening and the like. The terms "rationally selected" or "rationally designed" are meant to define compounds, which have been chosen based on the configuration of the interaction domains of the present invention. As will be understood by the person of ordinary skill, macromolecules having non-naturally occurring modifications are also within the scope of the term "molecule". For example, peptidomimetics, well known in the pharmaceutical industry and generally referred to as peptide analogs, can be generated by modelling as mentioned above. Similarly, in a preferred embodiment, the polypeptides of the present invention are modified to enhance their stability. It should be understood that in most cases this modification should not alter the biological activity of the interaction domain. The molecules identified in accordance with the teachings of the present invention have a therapeutic value in diseases or conditions in which the physiology or homeostasis of the cell and/or tissue is compromised by a high affinity protein interaction identified in accordance with the present invention. Alternatively, the molecules identified in accordance with the teachings of the present invention find utility in the development of more efficient agents, which can modulate such interactions.

Libraries of compounds (publicly available or commercially available, e.g., a combinatorial library) are well known in the art. Libraries of peptides are also available. Such libraries can be used to build an overlapping set of peptide sequences spanning a chosen domain, protein or part thereof.

As used herein, the recitation "indicator cells" refers to cells that express, in one particular embodiment, two interacting peptide domains of the present invention, and wherein an interaction between these proteins or interacting domains thereof is coupled to an identifiable or selectable phenotype or characteristic such that it provides an assessment or validation of the interaction between same. Such indicator cells can also be used in the screening assays of the present invention. In certain embodiments, the indicator cells have been engineered so as to express a chosen derivative, fragment, homolog, or mutant of these interacting domains. The cells can be yeast cells or higher eukaryotic cells such as mammalian cells (WO 96/41169). In one particular embodiment, the indicator cell is a yeast cell harboring vectors enabling the use of the two hybrid system technology, as well known in the art (4) and can be used to test a compound or a library thereof. In one embodiment, a reporter gene encoding a selectable marker or an assayable protein can be operably linked to a control element such that expression of the selectable marker or assayable protein is dependent on the interaction of the Protein A and Protein B interacting domains. Such an indicator cell could be used to rapidly screen at high-throughput a vast array of test molecules. In a particular embodiment, the reporter gene is luciferase or β-Gal.

In one embodiment, at least one of the two interacting proteins or domains of the present invention may be provided as a fusion protein. The design of constructs therefor and the expression and production of fusion proteins are well known in the art (4, 96). In a particular embodiment, both interaction domains are part of fusion proteins. A non-limiting example of such fusion proteins includes a LexA-Protein A fusion (DNA-binding domain-Protein A; bait) and a B42-Protein B fusion (transactivator domain-Protein B; prey). In yet another particular embodiment, the LexA-Protein A and B42-Protein B fusion proteins are expressed in a yeast cell also harboring a reporter gene operably linked to a LexA operator and/or LexA responsive element. Of course, it will be recognized that other fusion proteins can be used in such two hybrid systems. Furthermore, it will be recognized that the fusion proteins need not contain the full-length interacting proteins. Indeed, fragments of these polypeptides, provided that they comprise the interacting domains, can be used in accordance with the present invention, as evidenced with the peptide spanning method of the present invention.

Non-limiting examples of such fusion proteins include hemagglutinin fusions, gluthione-S-transferase (GST) fusions and maltose binding protein (MBP) fusions. In certain embodiments, it might be beneficial to introduce a protease cleavage site between the two polypeptide sequences which have been fused. Such protease cleavage sites between two heterologously fused polypeptides are well known in the art.

In certain embodiments, it might also be beneficial to fuse the interaction domains of the present invention to signal peptide sequences enabling a secretion of the fusion protein from the host cell. Signal peptides from diverse organisms are well known in the art. Bacterial OmpA and yeast Suc2 are two non limiting examples of proteins containing signal sequences. In certain embodiments, it might also be beneficial to introduce a linker (commonly known) between the interaction domain and the heterologous polypeptide portion. Such fusion protein find utility in the assays of the present invention as well as for purification purposes, detection purposes and the like.

For certainty, the sequences and polypeptides useful to practice the invention include, without being limited thereto, mutants, homologs, subtypes, alleles and the like. It shall be understood that generally, the sequences of the present invention should encode a functional (albeit defective) domain. It will be clear to the person of ordinary skill that whether an interaction domain, variant, derivative, or fragment thereof, of the present invention retains its function in binding to its partner can be readily determined by using the teachings and assays of the present invention and the general teachings of the art.

As exemplified herein below, the interaction domains of the present invention can be modified, for example by in vitro mutagenesis, to dissect the structure-function relationship thereof and permit a better design and identification of modulating compounds. However, some derivative or analogs having lost their biological function of interacting with their respective interaction partner may still find utility, for example for raising antibodies. Such analogs or derivatives could be used for example to raise antibodies to the interaction domains of the present invention. These antibodies could be used for detection or purification purposes. In addition, these antibodies could also act as competitive or non-competitive inhibitors and be found to be modulators of an interaction identified in accordance with the present invention.

A host cell or indicator cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting DNA may be maintained on a episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA. Transfection methods are well known in the art (4, 96). The use of a mammalian cell as indicator can provide the advantage of furnishing an intermediate factor, which permits or modulates the interaction of two polypeptides which are tested, that might not be present in lower eukaryotes or prokaryotes. Of course, an advantage might be rendered moot if both polypeptides tested directly interact. It will be understood that extracts from mammalian cells for example could be used in certain embodiments, to compensate for the lack of certain factors in a chosen indicator cell. It shall be realized that the field of translation provides ample teachings of methods to prepare and reconstitute different types of extracts.

In general, techniques for preparing antibodies (including monoclonal antibodies and hybridomas) and for detecting antigens using antibodies are well known in the art (12). The present invention also provides polyclonal, monoclonal antibodies, or humanized versions thereof, chimeric antibodies and the like which inhibit or neutralize their respective interaction domains and/or are specific thereto.

From the specification and appended claims, the term "therapeutic agent" should be taken in a broad sense so as to also include a combination of at least two such therapeutic agents. The DNA segments or proteins according to the present invention can be introduced into individuals in a number of ways. For example, erythropoietic cells can be isolated from the afflicted individual, transformed with a DNA construct according to the invention and reintroduced to the afflicted individual in a number of ways, including intravenous injection. Alternatively, the DNA construct can be administered directly to the afflicted individual, for example, by injection in the bone marrow. The therapeutic agent can also be delivered through a vehicle such as a liposome, which can be designed to be targeted to a specific cell type, and engineered to be administered through different routes.

For administration to humans, the prescribing medical professional will ultimately determine the appropriate form and dosage for a given patient, and this can be expected to vary according to the chosen therapeutic regimen (e.g. DNA construct, protein, molecule), the response and condition of the patient as well as the severity of the disease.

Compositions within the scope of the present invention should contain the active agent (e.g. protein, nucleic acid, or molecule) in an amount effective to achieve the desired therapeutic effect while avoiding adverse side effects. Typically, the nucleic acids in accordance with the present invention can be administered to mammals (e.g. humans) in doses ranging from 0.005 to 1 mg per kg of body weight per day of the mammal which is treated. Pharmaceutically acceptable preparations and salts of the active agent are within the scope of the present invention and are well known in the art (88). For the administration of polypeptides, antagonists, agonists and the like, the amount administered should be chosen so as to avoid adverse side effects. The dosage will be adapted by the clinician in accordance with conventional factors such as the extent of the disease and different parameters from the patient. Typically, 0.001 to 50 mg/kg/day will be administered to the mammal.

The methods and assays of the present invention have also been validated with Annexin. This protein is significantly different from P-glycoprotein in both structure and function. Consequently, together with the knowledge of protein chemistry and molecular biology, these validations support the utility of the instant assays and methods for all proteins (from viruses, living cells, animals, plants, etc.)

BRIEF DESCRIPTION OF THE DRAWINGS

Having thus generally described the invention, reference will now be made to the accompanying drawings, showing by way of illustration a preferred embodiment thereof, and in which:

FIG. 10 shows the sequence alignment of three binding regions of HP-gp1 and HP-gp3 linker domains. Alignment of HP-gp1 (SEQ ID NO: 15) and HP-gp3 (SEQ ID NO: 14) linker domains is shown using a single-letter code for amino acids. The regions of high binding affinities for HP-gp3 and HP-gp1 are shown in bold. Identical amino acids are shown by single letter code between the two aligned sequences. Conserved amino acids are indicated by plus (+) sign. The numbers on each side of the amino acid sequence of the linker domains refer to the amino acid sequence of human P-gp1 and 3 as in (90, 111).

FIG. 15 shows the helical wheel presentations of the high affinity binding region of HP-gp1 and HP-gp3 linker domains. The single-letter amino acid code for the high affinity binding region of HP-gp1 (SEQ ID NO: 12) and HP-gp3 (SEQ ID NO: 13) linker domains are shown. The positively charged amino acids on one side of the helix have been circled.

Other objects, advantages and features of the present invention will become more apparent upon reading of the following non-restrictive description of preferred embodiments with reference to the accompanying drawing, which is exemplary and should not be interpreted as limiting the scope of the present invention.

DESCRIPTION OF THE PREFERRED EMBODIMENT

Figure 1:
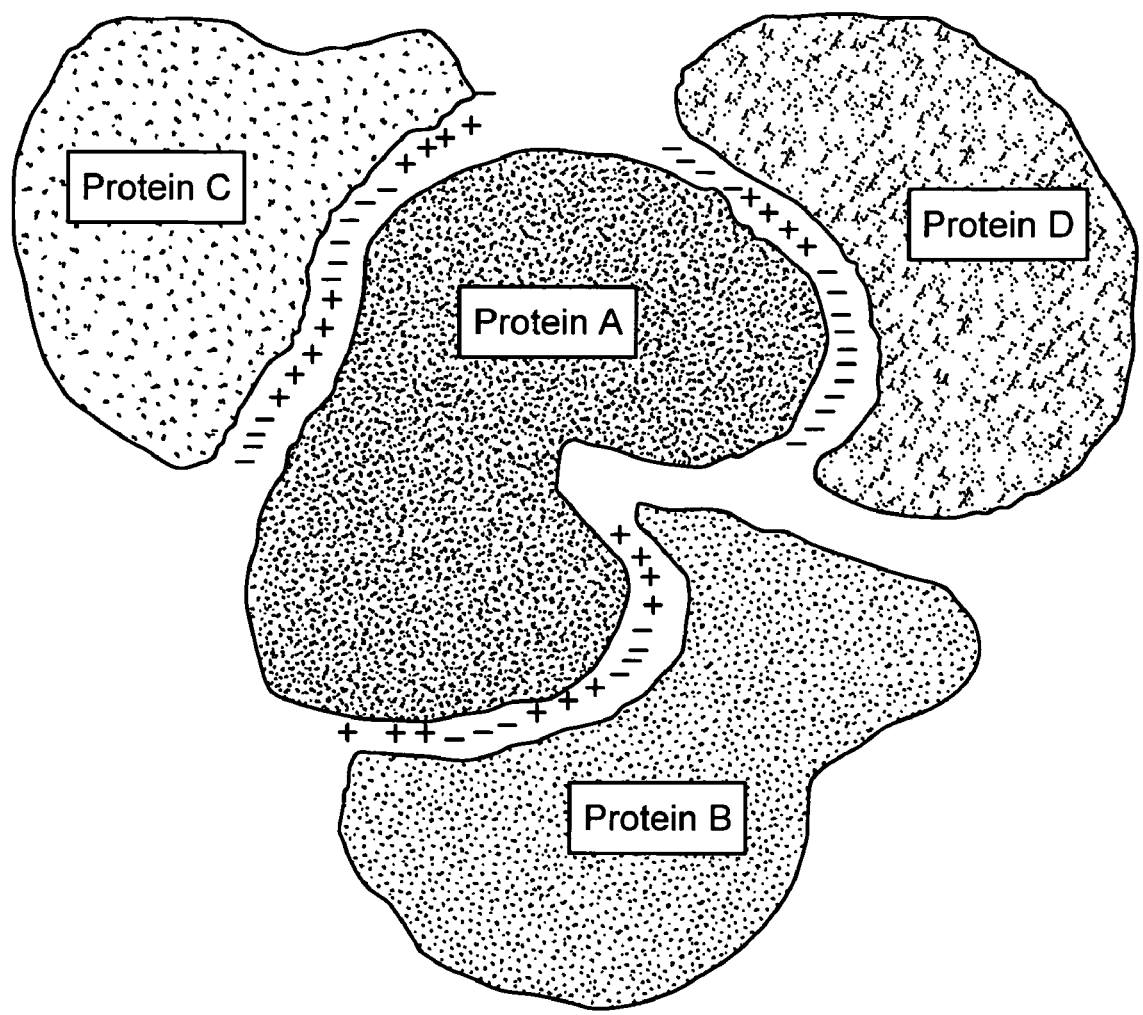
FIG. 1 shows the principle of protein-protein interaction. The plus sign (+) indicate the regions of high affinity binding. The minus signs (− −) indicate the regions of high-repulsive forces. As indicated in the text, interactions between two proteins are made up of discontinuous regions of high affinity binding and high-repulsive forces that are almost in equilibrium with high affinity binding being more favoured while proteins are together.
Figure 2A:
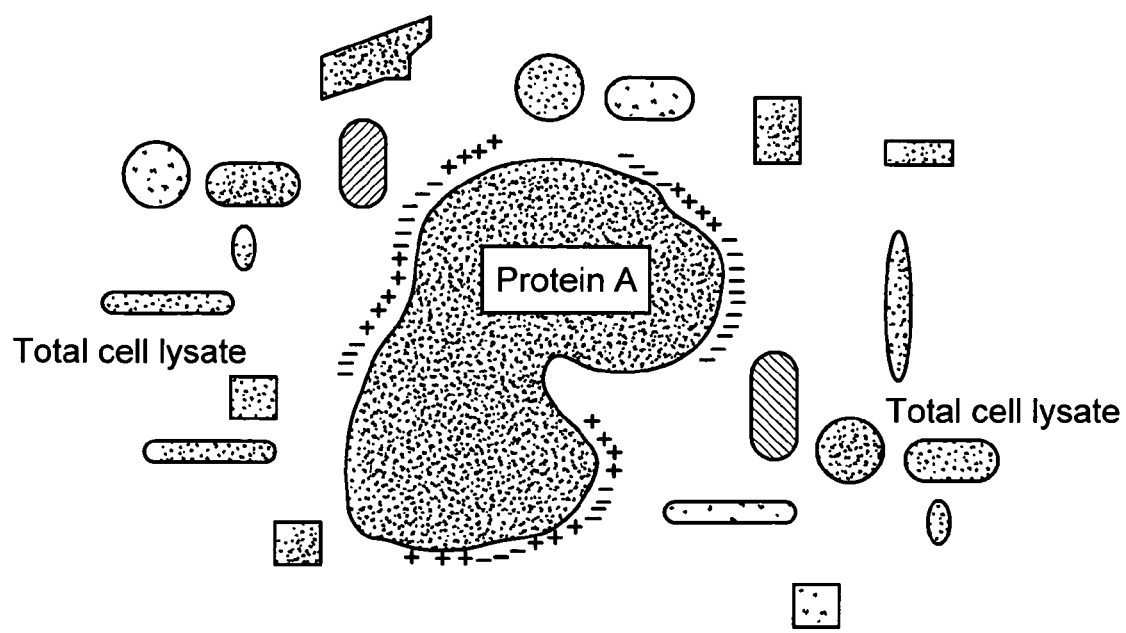
FIG. 2 is a schematic representation of a method of identification of high affinity binding sequences according to one embodiment of the present invention. 2A, the different shapes represent different proteins in a total cell lysate. The signs are like for FIG. 1. 2B, small overlapping peptides that cover the entire sequence (or a segment) of protein. A will be synthesized directly on derivatized wells of 96-well polypropylene plates. Following peptide synthesis, metabolically radiolabeled total cell lysate is added to each well containing the various peptides and incubated in an incubator buffer. 2C, the dark filled circles represent the radiolabeled proteins from total cell lysate isolated from metabolically radiolabeled cells added to all the wells of the 96-well plates to identify high affinity binding sequences on Protein A. 2D, after an extensive washing, the high affinity binding sequences (overlapping peptides from Protein A) are in those wells that bind radiolabeled proteins (in dark). Four high affinity binding sequences between Protein A and another protein(s) are identified in rows 1, 3, 6 and 8. The wells that contain the high affinity binding sequences are identified by radiolabeled counting and SDS-PAGE.
Figure 2B:
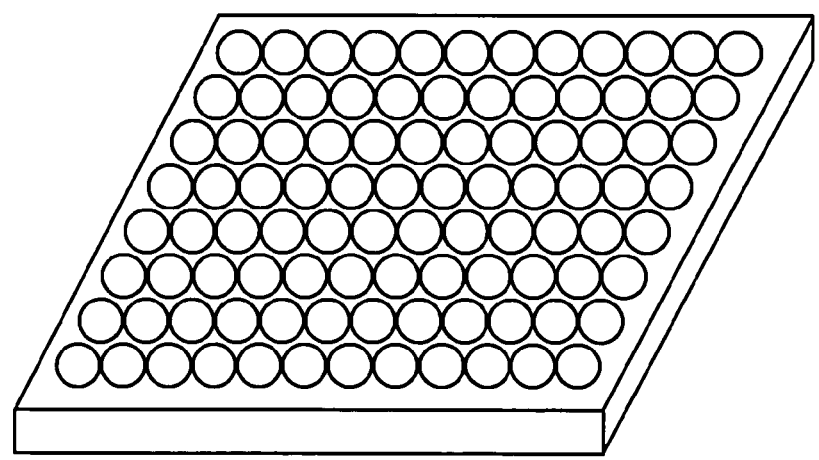
Figure 2C:
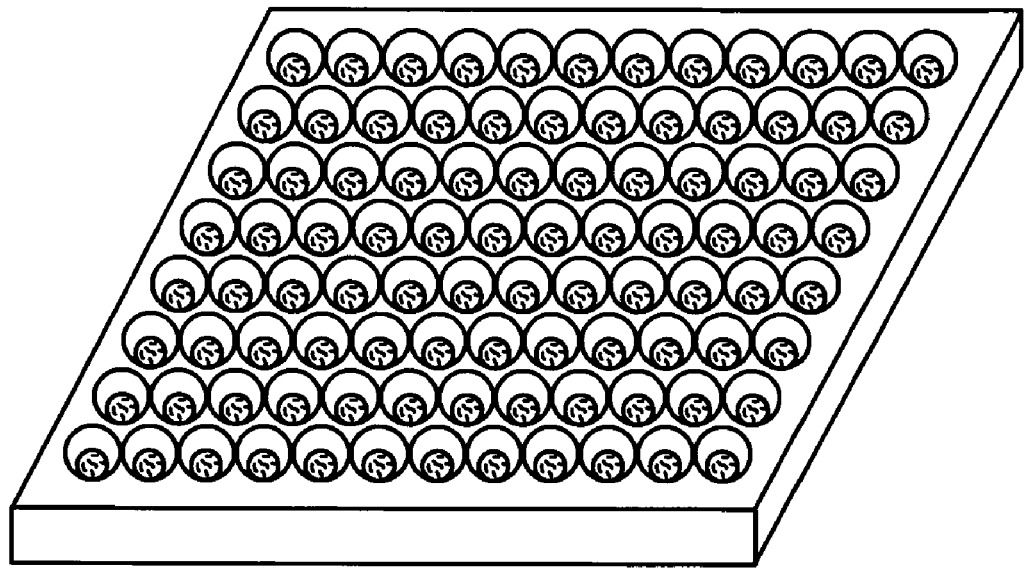
Figure 2D:
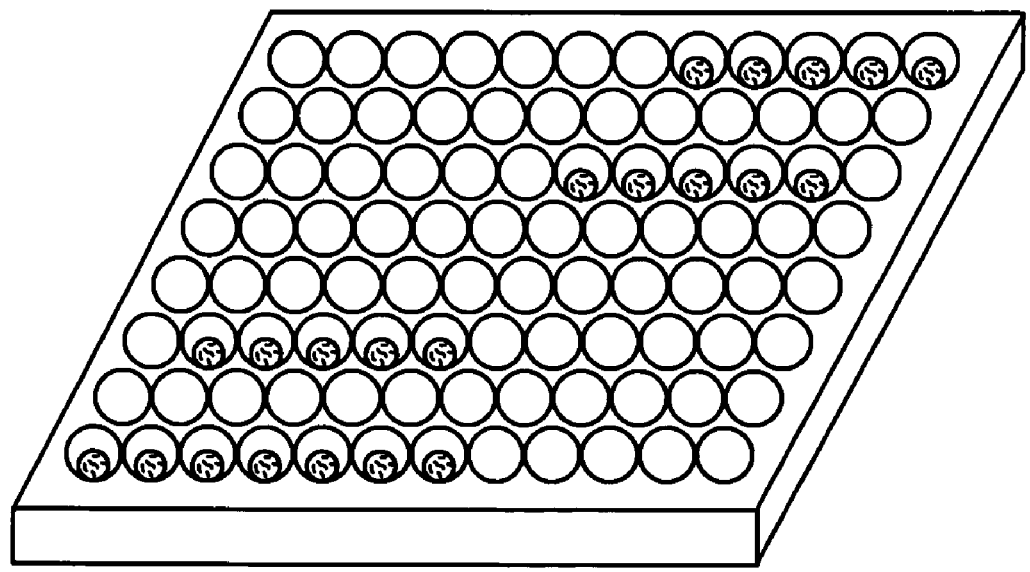
Figure 3A:
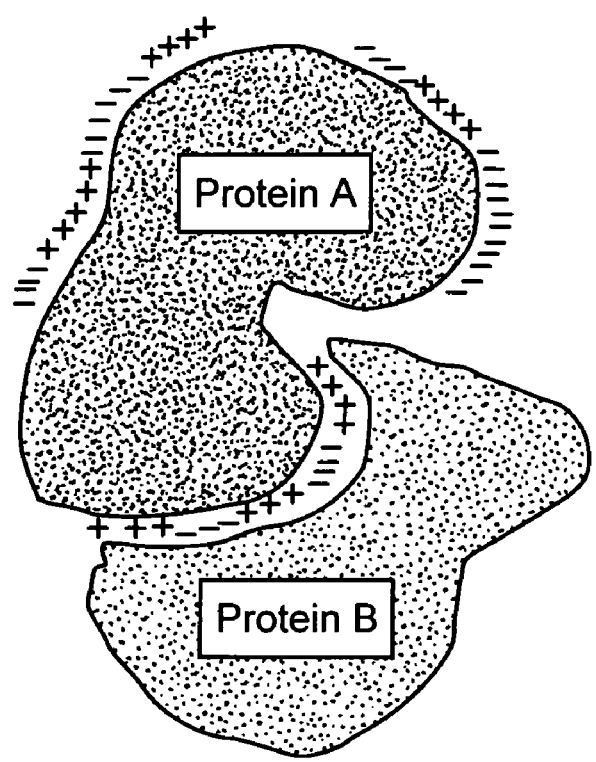
FIG. 3 is a schematic representation of a method of identification of high affinity binding sequences according to another embodiment of the present invention. 3A shows a schematic representation of the interaction between Protein A and Protein B. 3B, small overlapping peptides that cover the entire sequence (or a segment) of Protein A will be synthesized directly on derivatized wells of 96-well polypropylene plates. Following peptide synthesis, a radiolabelled Protein B (synthesized from in vitro transcription-translation reaction mix) are added to each well containing the various peptides and incubated in an incubation buffer. 3C, the dark filled circles represent the radiolabeled Protein B that has been added to all the wells of the 96-well plates to identify high affinity binding sequences on Protein A. 3D, after a washing procedure, the high affinity binding sequences are in those wells in which Protein B (radiolabeled protein in dark) is still bound to the peptides from Protein A.
Figure 3B:
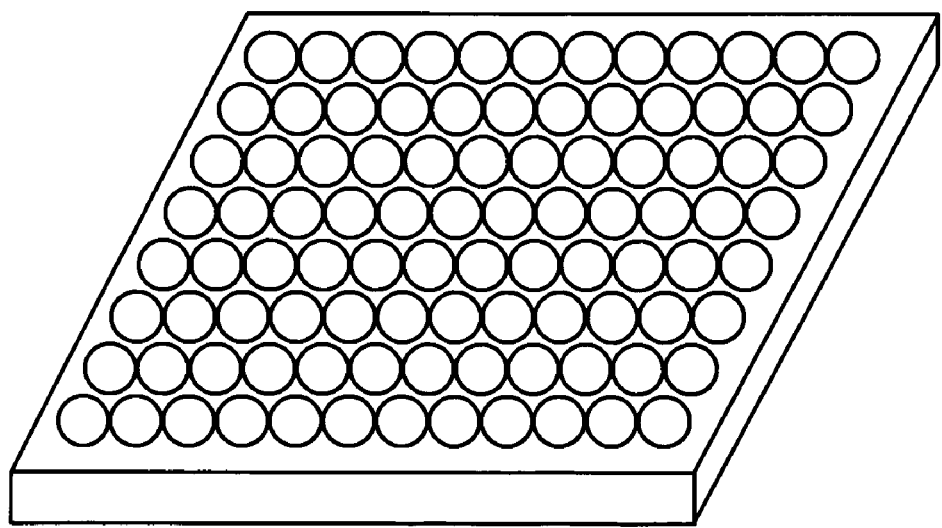
Figure 3C:
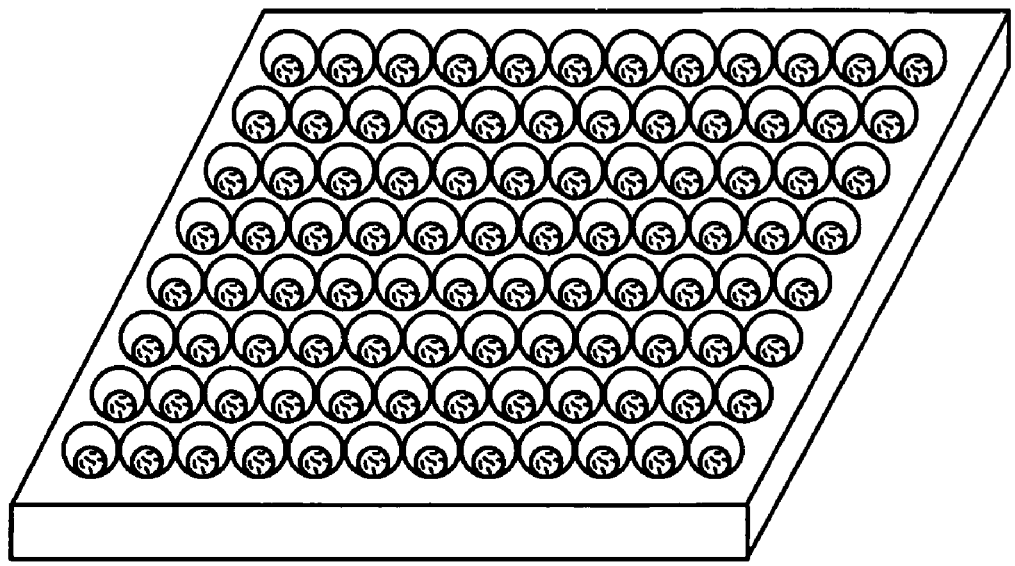
Figure 3D:
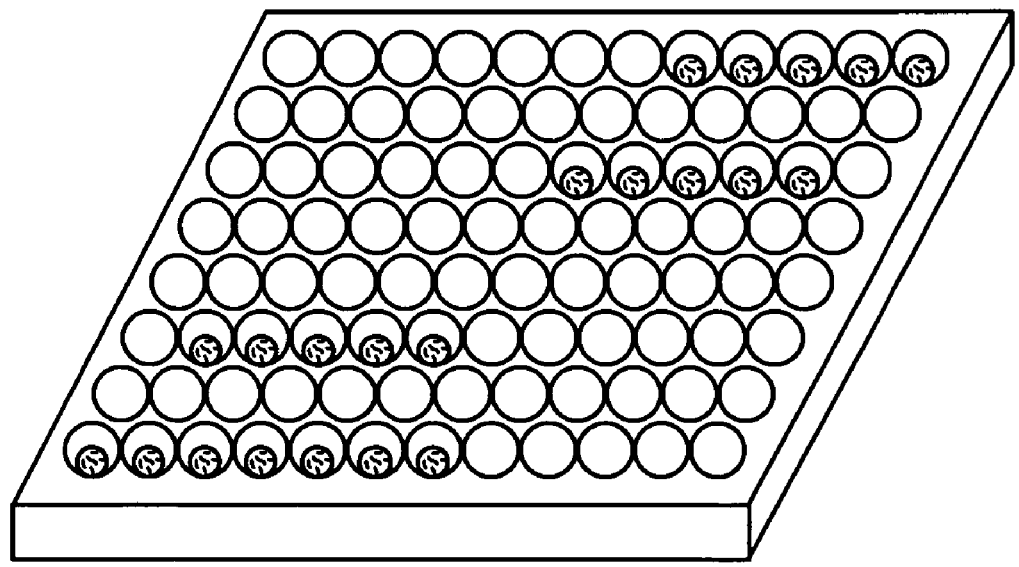
Figure 4A:
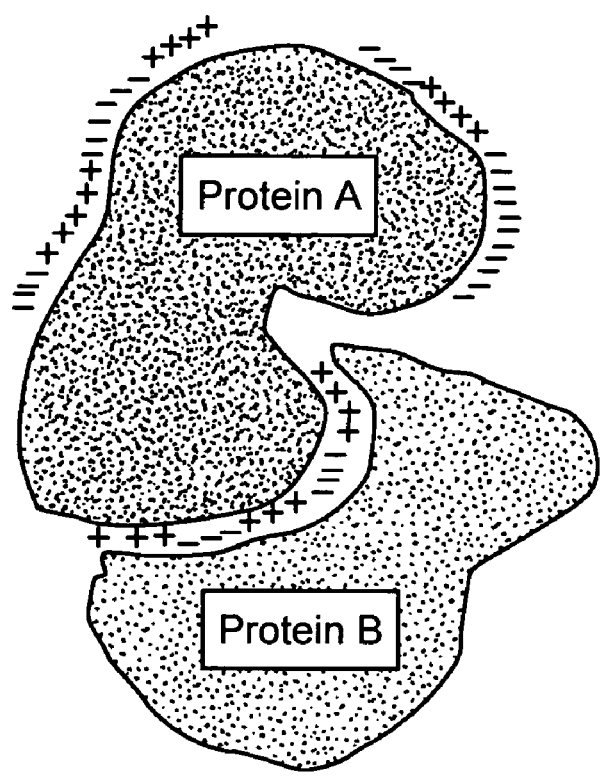
FIG. 4 is a schematic representation of a method of selection of drugs that specifically inhibit the binding of protein A to B according to one embodiment of the present invention. 4A shows a schematic representation of the interaction between Protein A and Protein B. 4B, peptides that encode high affinity binding sequences are used as LEAD sequences for the selection of specific drugs that inhibit the association between Protein A and Protein B and ultimately the function of the complex. To target the high affinity binding sequences that were identified in FIG. 2 or 3, peptides encoding one of the high affinity binding sequences are synthesized in every well of the 96-well plate. Grey circles represent one of four high affinity binding sequences identified in FIGS. 2 and 3. 4C, following the addition of a compound to be tested to each well of the 96-well plate, a radiolabeled Protein B are added to each of the wells. Of course, combinatorial libraries can be screened to identify drugs that bind specifically to the high affinity binding sequences of Protein A. As previously stated, radiolabeled Protein B from transcription-translation reaction mix are represented. Plates are washed and drugs that specifically bind to high affinity sequences of Protein A are found in those wells that do not contain radiolabeled Protein B. 4D, wells containing drugs/compounds that bind specifically to one of the high affinity binding sequence in Protein A and therefore prevent the binding of Protein B are identified by the absence of a dark circle (i.e., wells 28, 70 and 75). Selected drugs/compounds represent invaluable LEAD compounds that can be used in biological assays to confirm their mechanism of action. Validated drugs can proceed toward in vivo studies.
Figure 4B:
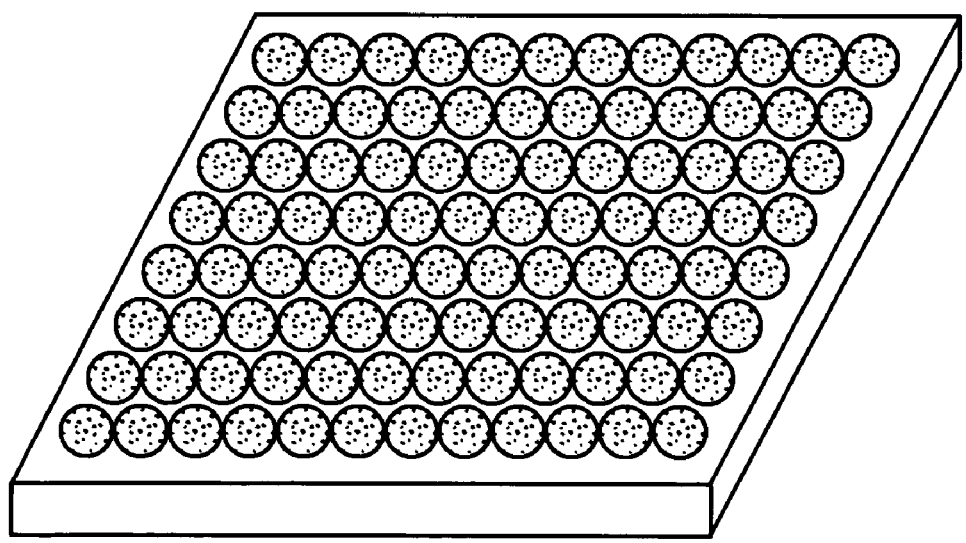
Figure 4C:
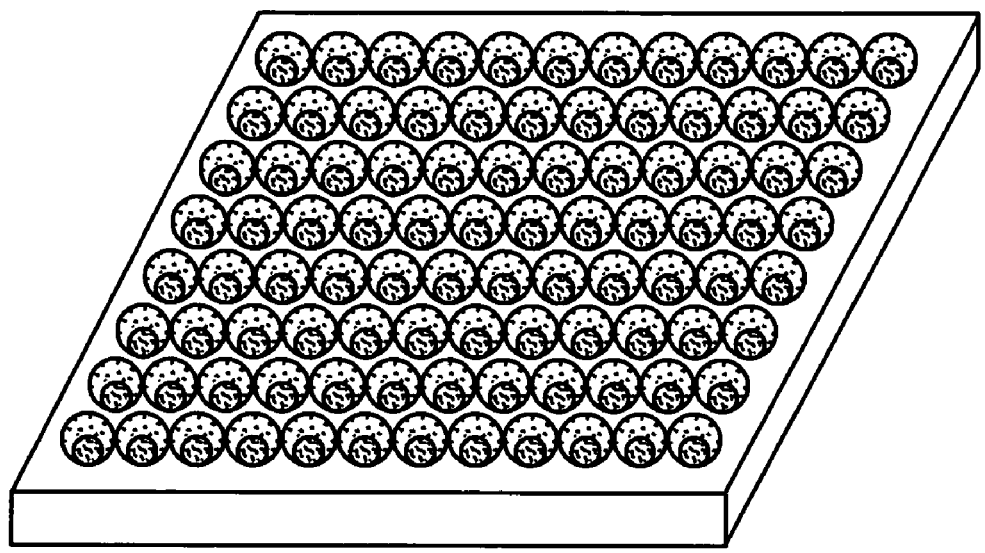
Figure 4D:
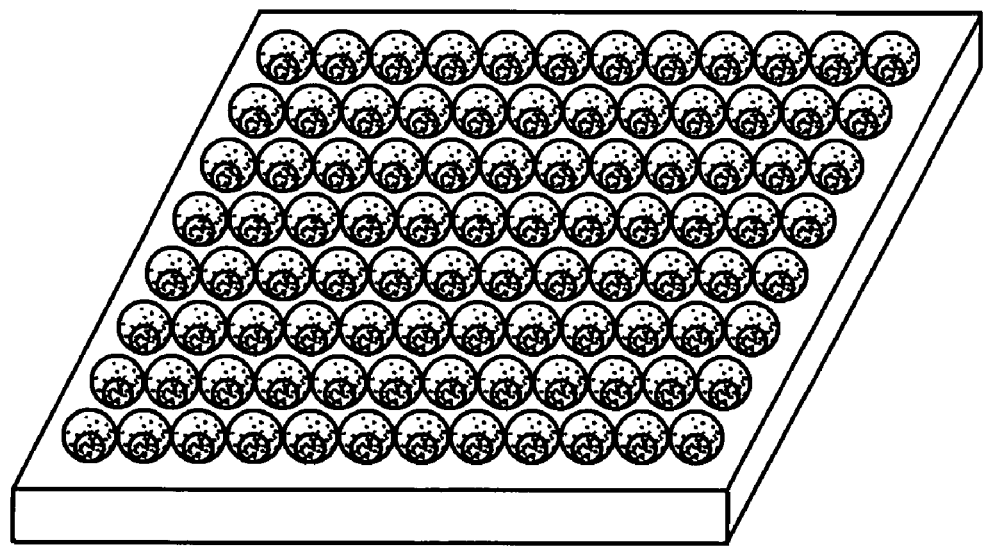

The function or functions of proteins is mediated through an interaction thereof with other cellular or extracellular proteins. Until now it was thought that interactions between two proteins involve large segments of polypeptides that have complementary amino acid sequences. However, it is not known how these complementary sequences mediate the interactions between proteins. In this application, a novel concept to explain the principle of protein-protein interactions is proposed. Briefly, interactions between any two or more proteins are mediated by strings of discontinuous sequences with high affinity binding and high-repulsive forces (see FIG. 1). The sum of these forces over the entire exposed sequence of proteins determines the nature and extent of the interactions between proteins. The sizes of these interacting domains can vary from 5 to 25 amino acids in length. The attractive forces between two small high affinity binding sequences are generally larger than the sum of all the high affinity binding and repulsive-forces between two proteins. Therefore, using the present approach, it is possible to isolate interacting proteins from a mixture of proteins using a short peptide (almost six amino acids) that encodes only the high affinity binding sequence. Indeed, with this in mind, it is now easy to see why many methods attempting to isolate interacting proteins have failed. The use of large fragments or proteins to isolate interacting proteins is less efficient since the sum of attractive/repulsive forces are much weaker than any string of attractive forces. The herein proposed principle is also consistent with the fact that protein-protein interactions can be modulated by post-translation modifications (e.g., by phosphorylation (29)) and the presence of other interacting proteins (60). Hence, the addition or loss of weak forces following post-translation modification can disrupt the tenuous balance between high affinity binding and high-repulsive forces that hold proteins together or prevent their association. Support for the magnitude of attractive forces between two high affinity binding sequences is demonstrated in antibody-antigen binding whereby the antigen can be only of a few amino acids (36, 37). Furthermore, numerous examples exist in biology where cellular interactions between proteins occur due to the presence of small consensus sequence of five to ten amino acids. Non-limiting examples of such small consensus sequences include the leucine zipper (63), and SH2 and SH3 binding sequences (63, 80). In addition to the domains of interactions between two or more proteins (indicated above), protein-protein interactions can have many measurable effects, such as: i) changes in the kinetic properties of one or both proteins (83, 84); ii) formation of new binding or functional sites (65, 104); and iii) the inactivation of function(s) (106, 114). In other words, a given protein could expose different functional domains or sequences in the presence (as opposed to the absence) of any interacting proteins. Thus, in the presence of protein B, protein A can expose other sequences not previously exposed for interactions with other proteins (65, 83, 84, 104, 106, 114). The latter concept is very important as it argues against the effectiveness of some structural studies (i.e., X-ray and NMR) in predicting functional or surface exposed domains from the resolved crystal structure of proteins. By enabling the measurement and the identification of potentially all the high affinity binding sites of a given protein, the present invention seeks to overcome the drawbacks of the results obtained from such structural studies.

Further to the above examples of protein-protein interactions, a subset of protein-protein interactions is dimerization. There is an abundance of examples in biology whereby protein-protein interactions are essential for activation or inhibition of function (59). Non-limiting examples of homo- or heterodimers include; growth factor receptors (52); membrane transport proteins (9, 36, 76); tumor suppressor proteins (72); and proteins that mediate apoptosis (87). In fact, dynamic dimerization is a common theme in the regulation of signal transduction. Some of the functional consequences of dimerization include, increased proximity for activation of single transmembrane cell surface receptors (e.g., EGF receptor (52)) and differential regulation by heterodimerization [e.g., BCL2 family of proteins (87)].

The protein concentration in living cells is very high and is in the range of 10–30 mg/ml. At this high protein concentration, most if not all proteins should interact precisely and specifically with other cellular proteins. Some of the interacting proteins act as inhibitors of function, while others may be activators (e.g., The BCL2-BAX family of proteins, (87)). Moreover, the cycling of a given protein between activator and inhibitor association will require the association-dissociation process to occur rapidly. For example, when protein X is associated with an inhibitor protein I, the domains (small sequences) that are required for the association of protein X with an activator protein A may not be easily accessible in the X-I complex. Therefore, current methods to identify associated protein (i.e., the two-hybrid system and similar approaches) may not be able to identify all associated proteins. In other words, current methods, when successful, may only identify some but not all functional domains and their associated proteins. By contrast, using the peptide scanning approach, the method of the present invention is capable of identifying all functional domains or high affinity interacting domains of protein X and its associated proteins. Once the associated proteins are identified, their biological functions as it relates to the target protein X can be tested. Thus, for a given interacting protein, should its interaction with one or many possible associated proteins prove to be important for function, the high affinity binding sequences (between protein X and Protein I or A) can be easily identified and can be used as a target site in a high throughput drug screening assays (see below) or other assays.

This invention includes the concept (described in FIGS. 1A–1D) that protein-protein interactions are made-up of discontinuous high affinity binding and high-repulsive forces scattered throughout the 3-D sequence of proteins and that these sequences can be isolated using one of many possible approaches indicated herein (e.g., the overlapping peptide approach). Although, in this application, the overlapping peptide approach is exemplified, other approaches can be envisioned that give similar results. It should be stressed that the approach described herein is immune to conformational changes resulting from interacting proteins that could effect other commonly used methods to identify protein-protein interactions (e.g., two-hybrid system, affinity blotting, and crosslinking). In the two hybrid system, for example, Protein A is fused with another protein sequence (the DNA-bound "bait" protein) and the other interacting protein is fused to the activation-domain containing "prey" protein. The fusion of interacting proteins to protein A could expose regions other than those found in the native conformation which will affect their interactions. Furthermore, the two-hybrid system has several disadvantages, some of which are listed below, i. The interaction of proteins is monitored in the nuclear milieu rather than the cytoplasm where most proteins are found.

ii. Proteins can be toxic when expressed in different cells or organisms.

iii. The interactions between two proteins in a complex in the two-hybrid system can sterically exclude the binding of other interacting proteins.

iv. The post-translational modification of one protein can exclude its interaction with other proteins.

v. The two-hybrid system does not allow the simultaneous identification of the precise amino acid sequences between two interacting proteins.

vi. The application of the two-hybrid system is associated with high percentage of false positives.

vii. The two-hybrid system cannot be easily applied to different cell types or tissues whereby different interacting proteins may be expressed (this can be a critical drawback of this system).

Method to Identify Interacting Proteins and Sites of Interactions for Protein A

The present approach and methodology used to identify discontinuous strings of sequences between two or more interactive proteins is a scanning overlapping peptide approach. Using this approach, a large number of short overlapping peptides which cover the entire amino acid sequence of the given protein, "the bait," are synthesized in parallel on an inert solid support (see FIG. 2). The rationale for synthesizing a large number of overlapping peptides as opposed to a discontinuous peptide library is based on the fact that one does not know a priori what exact sequence of a given protein will contain the high affinity binding sites and the repulsive sequences. Therefore, a discontinuous peptide approach will often lead to the presence of both high affinity binding sequences and repulsive sequences in the same peptide. Such peptides will not bind to potential interacting proteins with high affinity. Moreover, the use of overlapping peptides also provides internal controls for unspecific binding. For example, using overlapping peptides, the high affinity binding sequences will give a peak of signal when peptides within the high affinity domain will have the high affinity amino acid sequences but will lack amino acids which provide the repulsive forces (see FIG. 6 in Example I). Of course, if should be understood that the present invention is not dependent on a spanning of the full peptide sequence. Indeed, sub-region(s) of a protein can be used. In addition, overlapping peptides can be derived from a chosen domain of a protein. Also, it would be envisageable to probe an overlapping peptide side set of a first protein with an overlapping peptide set of a second protein.

Figure 6A:
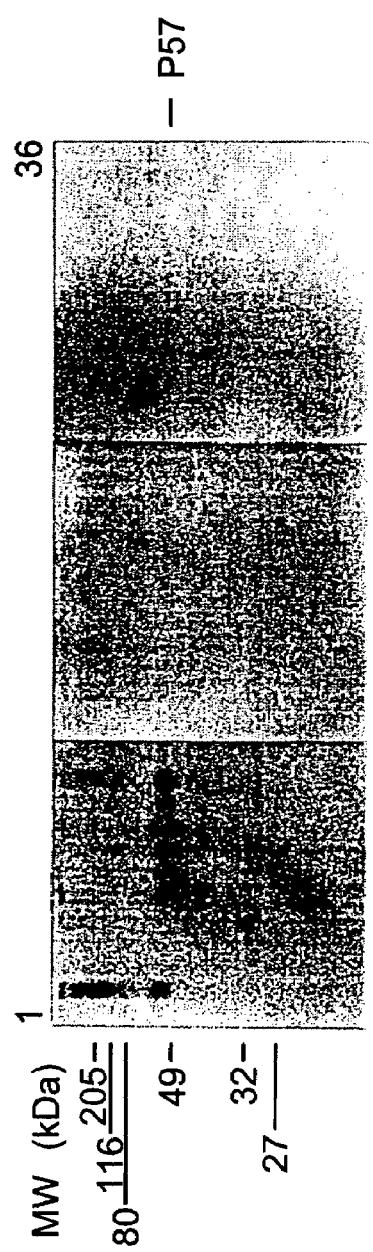
FIGS. 6A–C shows the protein binding to overlapping hexapeptides encoding HP-gp1 linker domain. Overlapping hexapeptides that encode the linker domain of HP-gp1 were synthesized on polypropylene rods and used to identify proteins that bind to these peptides. A total of 90 plus two control hexapeptides for HP-gp1 were incubated with total cell lysate from [$^{35}$S] methionine metabolically labeled cells (see methods). All bound proteins were eluted from the peptide-fixed rods and resolved on 10% SDS-PAGE. Lanes 1 to 92 show the [$^{35}$S] methionine bound proteins from HP-gp1. The migration of the molecular weight markers is shown to the left of gels.
Figure 6B:
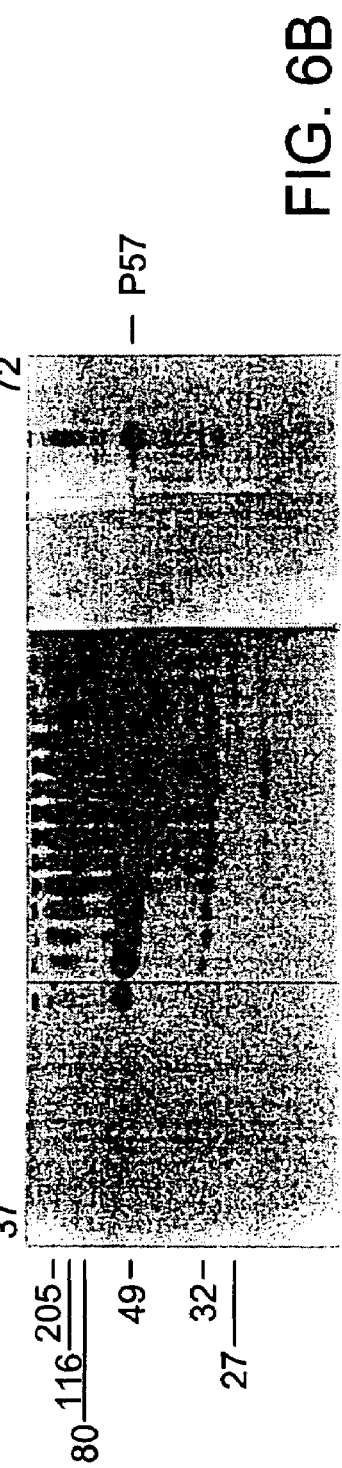
Figure 6C:
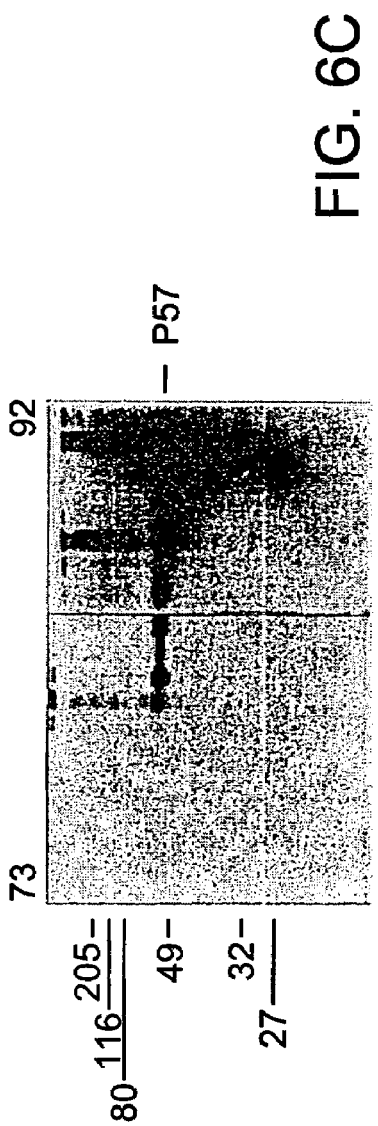

To demonstrate how one can use this approach of overlapping peptides as "a bait" to isolate interacting proteins "the prey" or "preys" from a mixture of total cell proteins, the following example can be considered. P-glycoprotein is a membrane protein (46) that confers resistance to anticancer drugs and therefore is responsible for the failure of chemotherapy. Although, P-glycoprotein has been shown to function by preventing the accumulation of chemotherapeutic drugs in tumor cells; the exact mechanism of how this protein functions and what are the associated proteins that modulate its function are not known. Thus, it is of interest to identify proteins that interact with P-glycoprotein, such as to enable an inhibition of binding between P-glycoprotein and its associated proteins, thereby potentially modulating its function in resistant tumor cells. In this example, it was of interest to identify those proteins which bind to the linker domain of P-glycoprotein. Thus, in this particular example, a domain of a chosen protein was used. The linker domain, encodes a region of about 90 amino acids. Thus, overlapping hexapeptides covering this entire linker sequence of P-glycoprotein were synthesized onto a solid support using standard F-moc chemistry (74). The covalently fixed peptides (on a solid support) were incubated with a total cell lysate isolated from cells metabolically with [$^{35}$S]methionine. The peptides and total cell lysate were incubated in the presence of a carrier substrate (1–3% bovine serum albumin, or 1–3% gelatin, 1–3% skim milk, etc.) for 18 hours at 4° C. Following this incubation period, the covalently fixed peptides were washed extensively with isotonic buffer. Any proteins from the radiolabeled total cell lysate which maintained their association with the overlapping hexapeptides following the washing step are eluted in SDS-contain sample buffer and analyzed by SDS polyacrylamide gel electrophoresis (SDS-PAGE) (62). The presence of radiolabeled proteins on SDS polyacrylamide gels following gel drying and signal enhancement, provides the following information:

1) those specific overlapping peptides represent high affinity binding sequences in the P-glycoprotein linker domain (or other chosen domains or non-chosen domains); and 2) the proteins bound to the specific overlapping peptides are associated proteins (see FIG. 6).

The associated proteins which bound to the high affinity binding sequences, can be isolated in large quantities for the purpose of determining their identity by N-terminal amino acid sequencing by Edman degradation (27) or the like. Briefly, the sequences of the overlapping peptides that bound a given protein are resynthesized on a solid support and kept fixed thereto. Total cell lysate from [$^{35}$S]methionine metabolically-radiolabeled cells is added to the solid support containing the fixed high affinity sequence peptides and incubated as described above. Following washing steps to remove unbound material, the associated protein is isolated in large amounts following an elution step with SDS-containing buffers (see below). The purified associated protein is now ready for amino acid sequencing. Of course, should further purification steps be required, they are well known to the skilled artisan. The purified protein is run on SDS polyacrylamide gels and the resolved protein is transferred to PVDF membrane as previously described (108). Other methods for amino acid sequence determination can also be easily applied (27, 33).

Method to Identify the Amino Acid Sequences Between Two Interacting Proteins

The same concept as described above can be applied if one is only interest in identifying the high affinity binding sequences between two proteins. A non-limiting example of such two proteins are the regions of interactions between p53 and MDM (28, 103). Specifically therefore, the purpose of this exercise is to identify the high affinity binding sequences between proteins A (p53) and protein B (MDM) in order to use these sequences as target sites for the identification of compounds that modulate this interaction and more particularly for the development of drugs. Thus, in one embodiment, when a given drug is bound to one of these high affinity binding sites on protein A, it will prevent the formation of the active complex (protein A+B) and therefore inhibit the functions of the complex. To isolate the string of high affinity binding sequences between Protein A and B (see FIG. 3), small overlapping peptides (5 to 7 amino acids) that cover the entire amino acid sequence of protein A, "the bait" will be synthesized in parallel onto a solid support (as mentioned above and described in more detail in Example 3). Note that, in this particular embodiment, only the primary amino acid sequence of protein A, "the bait," is needed. Once the peptides are synthesized (peptide synthesis is done parallel on a solid support in 96-well plates), an enriched and radiolabeled full-length protein B (the radiolabeled protein B is easily obtained from in vitro transcription-translation reactions), (118) "the prey," is added to each well of the 96-well plate that contain the covalently fixed overlapping peptides. The peptides encoding protein A are incubated with radiolabeled protein B to allow for binding to occur. Following an incubation period (5 to 24 hours), unbound radiolabeled protein B will be removed by extensive washing in isotonic buffer. Any overlapping peptides which bound to radiolabeled protein B will be eluted in the presence of denaturing agents. The eluant from each of the 96-well plates are analyzed for the presence of radiolabeled protein B by running the samples by SDS-PAGE (62). High affinity binding peptides will be identified as those that retain the radiolabeled Protein B.

The use of metabolically radiolabeled proteins as "the prey" to interact with the overlapping peptides of "the bait" increases the sensitivity of this technique and allows the identification of interacting proteins with binding affinities of $10^{-10}$–$10^{-12}$ M for a standard 50 kDa protein which encodes one to ten radiolabeled methionine residues (82).

Method to Use High Affinity Binding Sequences in High Throughput Assays to Screen for Lead Compounds The approach, described herein, to identify high affinity binding sequences or target sites for drug development can also be used in high throughput assays to screen for small molecules from combinatorial libraries. For example, to select drugs that specifically inhibit the binding of protein A to B (see FIG. 4), one or more target sites (the high affinity binding sequences) are synthesized in each of the 96-well plates as described earlier. In this example (FIG. 4) the same high affinity binding sequence is synthesized in all of the wells. To each well containing the high affinity binding sequence, one or more small molecules from combinatorial library are added. Following the addition of drug(s), a radiolabeled protein B from an in vitro transcription-translation mix, for example, is added and allowed to incubate as indicated above. Following several washes, bound protein B is eluted with SDS-sample buffer. Wells containing radiolabeled protein B indicates that the drug had no effect on the binding between the high affinity binding sequence and protein B. Alternatively, if one or more wells do not contain radiolabeled protein B in the presence of a drug, then that drug has inhibited the interactions between the high affinity binding sequence on A and protein B. Hence, the latter drug is a good LEAD compound. These drugs can now enter the second phase of their analysis to determine if they prevent the formation of the active complex of full length protein A and B. Active drugs that are identified will be tested in vivo to further confirm their mechanism of action. In this manner, more specific drugs with fewer or no side-effects will be developed.

The latter point provides an advantage since most proteins have more than one biological function. For example, if protein A interacts with itself, it will do one function, while the same protein interacting with a different protein will do a different function. Moreover, protein A, when part of a given complex of associated proteins, will mediate several functions, inhibiting the interactions between protein A and B, while leaving the interactions between proteins A and C, D, or F intact will inhibit one or few cellular pathways. By contrast, inhibiting the function of protein A will inhibit the functions of the entire complex. In this respect, the identification, isolation and development of drugs that will inhibit specifically interactions between two proteins within a complex of proteins should result in more specific drugs with fewer side effects. In addition, as different proteins are differentially expressed in different tissues or organs, the composition of a given protein complex will be different between different tissues. Hence, the approach of developing drugs that inhibit protein-protein interactions will also lead to drugs that are organ or tissue-specific.

Of course, it will be understood that the present invention also provides quantitative assays to measure the protein-protein interaction and the modulation thereof by compounds.

In conclusion, the approach described in this application for the identification interacting proteins, the precise amino acid sequence between interacting proteins, and targeting of such specific sequences in proteins with drugs that inhibit protein-protein interactions has tremendous potential in dictating future drug discovery in the pharmaceutical industry.

The present invention is illustrated in further detail by the following non-limiting examples.

EXAMPLE 1

P-glycoprotein Binding to Tubulin is Mediated by Sequences in the Linker Domain

The successful treatment of cancer patients with chemotherapeutic drugs is often limited by the development of drug-resistant tumors. Tumor cell lines selected, in vitro, with a single anticancer drug become resistant to a broad spectrum of chemotherapeutic drugs, termed multidrug resistant (or MDR) tumor cells (for review, (21, 45, 66). Moreover, the expression of MDR in these tumor cells has been associated with the overexpression of two membrane proteins; the MDR1 P-glycoprotein (P-gp) and the multidrug resistance-associated protein (MRP1) (21, 45, 66). Both P-gp and MRP are members of a large family of membrane transporter proteins known as ATP binding cassette proteins or ABC membrane transporters (54). Although, the structure of P-gp1 remains a matter speculation (91), cumulative topological evidence suggest a tandemly duplicated structure of six transmembrane domains and a large cytoplasmic domain encoding an ATP binding sequence (58, 68). The two halves of P-gp1 are linked by a stretch of 90 residues rich in polar or charged amino acids, termed the "linker domain."

The P-gp gene family is made up of three structurally similar isoforms in rodents (classes I, II, and III) and two isoforms in humans (classes I and III) (20). Gene transfer studies suggest functional differences among these structurally similar isoforms. For example, only the P-gp isoforms of classes I and II confer the MDR phenotype (25, 111), while the class III isoforms do not (11, 98). The class III isoforms mediate the transfer of phosphatidylcholine from the inner to the outer leaflet of the plasma membrane (i.e., "flipase") (92, 100). In normal tissues, P-gp distribution is restricted mainly to tissues with secretory functions (79, 116). Its polarized localization to apical surfaces facing a lumen in the adrenal gland, liver, kidney intestine suggests a normal transport or detoxification mechanism. Moreover, hematopoietic stem cells and specific lymphocyte subclasses also express high levels of P-gp (49). The normal function or substrate(s) of the classes I and II remain undefined; however, the disruption of the class I or/and II genes from the mouse genome results in the accumulation of cytostatic drugs or lipophilic compounds in most normal tissues, but more strikingly in the brain (99, 100). Based on these results it is speculated that the normal function of P-gp (the class I and II or the MDR causing P-gp) is detoxification similar to that seen in MDR cells, especially at the blood brain barrier (57).

High levels of P-gp have been found in many intrinsically drug resistant tumors from colon, kidney, breast and adrenals as well as in other tumors which had acquired the MDR phenotype after chemotherapy (for example, in acute non-lymphoblastic leukemia) (22, 32, 35, 47, 53, 78). Several studies have now established an inverse correlation of P-gp expression and the response to chemotherapy (5, 89, 113). Further, Chan et al. (16, 17) have shown that P-gp expression was prognostic of MDR and durable response in childhood leukemia, soft tissue sarcomas and neuroblastomas of children. In light of these studies there appears to be convincing evidence, at least in some cancers, that P-gp levels predict the response to chemotherapeutic treatment.

Direct binding between P-gp and various lipophilic compounds has been demonstrated using photoactive drug analogues (77, 93, 94). Certain compounds which bind to P-gp were shown to reverse the MDR phenotype presumably by competing for the same drug binding site in P-gp (34, 38). These compounds, which have been collectively labeled as MDR-reversing agents, include verapamil, quinidine, ivermectin, cyclosporins, and dipyrimadol analogues to name but few (34, 38). Clinical trials using MDR-reversing agents (e.g., verapamil or quinidine) have shown some response in tumors that were otherwise non-responsive to chemotherapy (23, 44, 117). However, high pharmacological toxicity associated with several MDR-reversing agents has prevented their use at an effective concentration (67). A better clinical response has been observed using other MDR-reversing agents (i.e., cyclosporin A and its non-immunosuppressive analog PSC833); however toxic effects have also been seen with cyclosporins (101, 115).

P-gp was shown to be a substrate for protein kinases C and A (2, 9). Moreover, it has been demonstrated that agents which modulate protein kinase C activity, modulate P-gp phosphorylation and its MDR-mediate phenotype (7, 13). In one study (31), PMA phorbol ester (a protein kinase C activator) was shown to increase the MDR phenotype and drug efflux in MCF7 breast cancer cells. In another study (6), sodium butyrate treatment of SW620 human colonic carcinoma cells was shown to result in a large increase in P-gp expression without a concomitant increase in drug-resistance or efflux. Interestingly, P-gp in SW620 cells was also shown to be poorly phosphorylated following sodium butyrate treatment (6). Taken together, the lack of transport function of P-gp in SW620 cells was not clear, however mutations of P-gp phosphorylation sites within the linker domain was shown not to affect its drug transport function (40). By contrast, protein kinase C modulation of serine/threonine residues in the linker domain regulated the activity of an endogenous chloride channel and thus suggests that P-gp is a channel regulator (41, 110). Thus, although, it remains unclear what functions the linker domain of P-gp1 mediates, it was of interest to identify the proteins that interact with linker domain using an in vitro assay. The latter assay is based on the novel understanding of protein interactions provided by the present invention. The results show hereinbelow that three sequences in the linker domain bind to proteins with apparent molecular masses of ~80 kDa, 57 kDa and 30 kDa. Purification and partial N-terminal amino acid sequencing of the 57 kDa protein showed that it encodes the N-terminal amino acids of α and β-tubulins.

Thus, using a protein domain as an example of a validation of the power of the present invention, it was demonstrated that: i) this domain is bound specifically to proteins; ii) the specifically binding proteins can be formally identified; and iii) the sequence responsible for the specific binding of these proteins formally identified (together with the interacting domain of this binding protein, if derived).

EXAMPLE 2

Materials

[$^{35}$S] methionine (1000 Ci/mmol; Amersham Life Sciences, Inc.) and [$^{125}$I] goat anti-mouse antibody were purchased from Amersham Biochemical Inc. Protein-A Sepharose-4B was purchased from Bio-Rad Life Science. All other chemicals used were of the highest commercial grade available.

EXAMPLE 3

Peptide Synthesis

Pre-derivatized plastic rods, active ester and polypropylene trays were purchased from Cambridge Research Biochemicals (Valley Stream, N.Y.). Peptides were synthesized on solid polypropylene rods as previously described (36, 37). Briefly, the F-moc protecting group on the prederivatized polypropylene rods as solid support (arranged in a 96-well formate) was removed by incubation with 20% (v/v) piperidine in dimethylformamide (DMF) for 30 minutes with shaking. Following the deprotection of the β-alanine spacer on the polypropylene rods, Fmoc protected amino acids were dissolved in HOBt/DMF and added to the appropriate wells containing deprotected rods. Coupling of amino acids was allowed to take place for 18 hours at room temperature after which the rods were washed in DMF (1×2 minutes), methanol (4×2 minutes), and DMF (1×2 minutes). The coupling of the second amino acid required the deprotection of the F-moc amino protecting group of the first amino acid and incubation of the rods with the second preactivated F-moc-protected amino acids (pentafluorophenyl derivatives). The reaction was allowed to proceed for 18 hours, and the rods were removed and washed as indicated above. The same steps were repeated for each amino acid coupling until the sixth amino acid was coupled. Following the last coupling step, the F-moc N-terminal protecting group was removed with 20% piperidine/DMF and the free amino group acetylated for 90 minutes in an acetylation cocktail containing acetic anhydride:diisopropylethylamine (DIEA):DMF (50:1:50 v/v/v). The side chain protecting groups of the N-terminal acetylated hexapeptides onto the polypropylene rods were removed by incubation in a cleavage mixture containing trifluoroacetic acid:phenol: ethandithiol (95:2.5:2.5 v/v/v) for 4 hours at room temperature. After the cleavage step the rods were washed with dichloromethane (DCM) and neutralized in 5% (v/v) DIEA/DCM. The deprotected peptide-coupled rods were washed in DCM, methanol and vacuum dried for 18 hours.

EXAMPLE 4

Tissue Culture and Metabolic Labeling of Cells

Drug sensitive (CEM) and resistant (CEM/VLB$^{1.0}$) cells were cultured in α-MEM media supplemented with 10% fetal calf serum (Hyclone, Inc.) as previously described (8). All cells were examined for Mycoplasma contamination every three months using the Mycoplasma PCR kit from Stratagene Inc. (San Diego, Calif.). For metabolic labeling of cells, CEM or CEM/VLB$^{1.0}$ cells at 70–80% confluency were metabolically labeled with [$^{35}$S] methionine (100 µCi/ml) for 6 hours at 37° C. in methionine-free α-MEM media.

EXAMPLE 5

Cell Extraction and Binding Assay

Following metabolic labeling of proteins with [$^{35}$S] methionine, cells were washed 3 times with phosphate buffered saline (PBS) and resuspended in hypotonic buffer (10 mM KCl, 1.5 mM MgCl$_2$, 10 mM Tris-HCl, pH 7.4) containing protease inhibitors (2 mM PMSF, 3 µg/ml Leupeptin, 4 µg/ml pepstatin A and 1 µg/ml aprotinin) and kept on ice for 30 minutes. Cells were lysed by homogenization in a hypotonic buffer and the cell lysate was sequentially centrifuged at 6000×g for 10 minutes. Following the latter centrifugation, the supernatant was removed and made 0.5 M NaCl final concentration from a stock solution of 4 M NaCl. The cell lysate was incubated on ice for 30 minutes. The sample was mixed and brought back to 0.1 M NaCl final concentration. The cell lysate was centrifuged for 10 minutes at 15,000×g at 4° C. The latter supernatant was removed and recentrifuged at 100,000×g for 60 minutes in a Beckman ultracentrifuge using SW55 rotor. The amount of protein in the above samples was determined by the method of Lowry (69).

For a binding assay, [$^{35}$S] methionine labeled proteins from total cell lysate were mixed with equal volume of 3–6% BSA in phosphate buffered saline (PBS) and incubated with overlapping hexapeptides covalently fixed to polypropylene rods. The peptides and total cell lysate were incubated overnight at 4° C. The rods were then removed and washed four times in PBS. The bound proteins were eluted by incubating the peptide-fixed rods in 1×SDS sample buffer for 60 minutes at room temperature with shaking. The peptides-fixed rods, were regenerated by incubation in PBS, containing 2% SDS and 1 mM β-mercaptoethanol at 65° C. in a sonicator for 30 minutes. Following the latter incubation, the rods were washed for five minutes in 65° C. ionized water and two minutes in 65° C. methanol. The peptides-fixed rods are now ready for the next round of screening. In cases where the effects of various detergents on binding was tested, [$^{35}$S] methionine labeled proteins from total cell lysate were mixed with equal volume of 3% BSA in phosphate buffered saline containing KCl (300 mM to 1200 mM), SDS (0.12% to 2%), or CHAPS (20 mM to 160 mM) and incubated with covalently fixed peptides as described above.

EXAMPLE 6

Polyacrylamide Gel Electrophoresis and Western Blotting

Protein fractions (100–150 µl) were resolved on SDS-PAGE using the Laemmli gel system (62). Briefly, proteins were dissolved in 1×solubilization sample buffer I (62.5 mM Tris-HCl, pH 6.8, containing 2% (w/v) SDS, 10% (w/v) glycerol and 5% β-mercaptoethanol) and samples were electrophoresed at constant current. Gel slabs containing the resolved proteins were fixed in 50% methanol and 10% acetic acid. Polyacrylamide gels containing [$^{35}$S] methionine proteins were exposed to Kodak x-ray film following a thirty-minute incubation in an Amplify™ solution (Amersham Inc.).

Alternatively, proteins were transferred to nitrocellulose membrane in Tris-glycine buffer in the presence of 20% methanol for Western blot analysis according to the procedure of Towbin et al. (108). Nitrocellulose membrane was incubated in 5% skim milk/PBS prior to the addition of anti-α or anti-β tubulin monoclonal antibodies (0.5 μg/ml in 3% BSA; Amersham, Inc.). Following several washes with PBS, the nitrocellulose membrane was incubated with goat anti-mouse peroxidase-conjugated antibody and immunoreactive proteins were visualized by chemiluminescence using ECL method (Amersham, Inc.).

EXAMPLE 7

Protein Purification and N-terminal Sequencing

The 57 kDa associated protein was purified using a block of polypropylene rods with two high affinity binding peptides. Briefly, the peptide-fixed rods were incubated with total cell lysate as indicated above; however, in this case the carrier substance was gelatin (1%). The bound proteins were eluted in 100 mM phosphate buffer, pH 7.4 containing 2% SDS and 0.1% β-mercaptoethanol. The eluted proteins were precipitated by mixing with 9 volumes of ice cold ethanol and incubated at −20° C. Following a high speed centrifugation of the latter sample (15 minute centrifugation at 15,000×g, at 4° C.), the precipitated proteins were resuspended in 1% SDS in PBS and mixed with equal volume of 2×SDS Laemmli sample buffer (62). Protein samples were resolved by 10% SDS-PAGE and transferred to PVDF membrane. The migration of the 57 kDa band was visualized by staining the PVDF membrane with Ponceau S. The PVDF membrane containing the 57 kDa band was excised and submitted to the protein sequencing facility at the Biotechnology Service Centre in Toronto, Ontario. Amino acid sequencing of peptides was performed according to the method of Edman and Begg (27) using an applied biosystems gas-phase Model 470A sequenator™ according to the procedure described by Flynn (33).

EXAMPLE 8

Identification of P-gp Interacting Proteins

Figure 5:
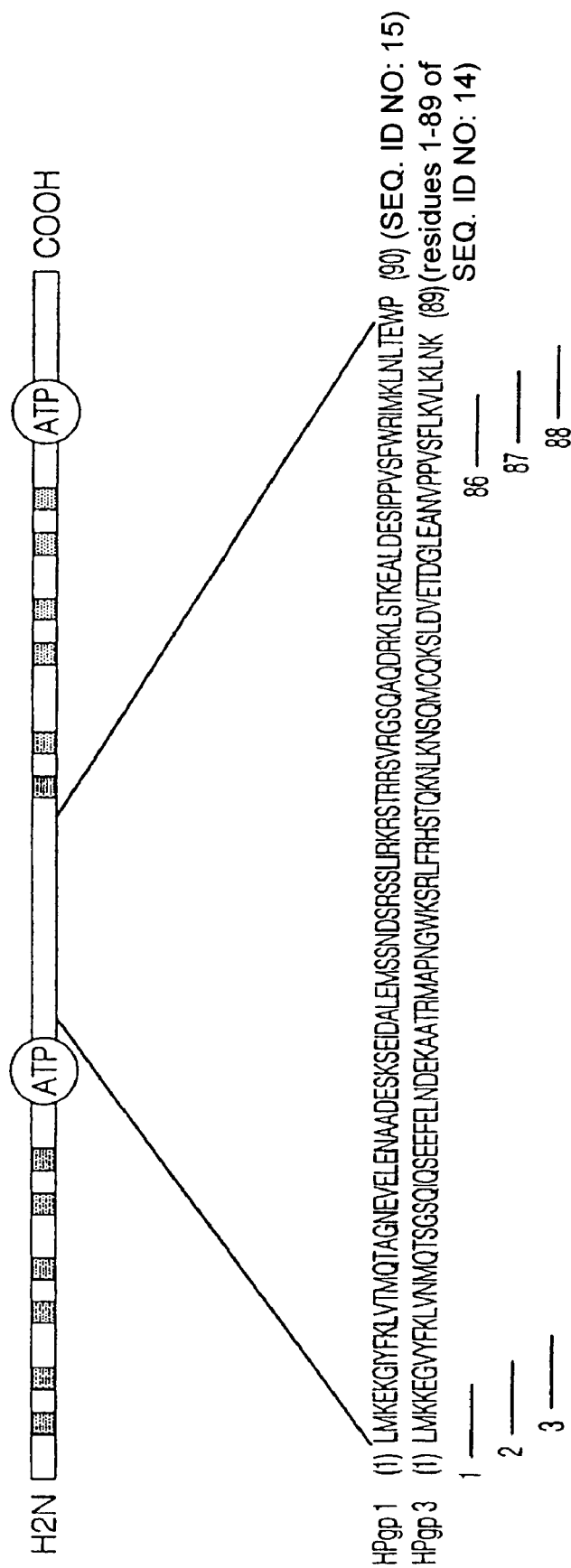
FIG. 5 shows a P-glycoprotein predicted secondary structure and amino acid of the linker domain. A schematic representation of the predicted secondary structure of P-gp. The twelve filled squares represent the twelve putative transmembrane domains. The two ATP binding domains are represented by two circles in the N- and C-terminal halves of P-gp. The inset represents the linker domain. The amino acid sequence of the linker domains of Human P-gp 1 (HP-gp1) and HP-gp3 is indicated as a single-letter amino acid code. The numbers in brackets at the beginning and end of each amino acid sequence of HP-gp1 (SEQ ID NO: 15) and HP-gp3 (residues 1–89 of SEQ ID NO: 14) shows the length of the linker domains (1–90 and 1–89 for HP-gp1 and HP-gp3, respectively). The numbered lines underneath the amino acid sequence show the sequences of the overlapping hexapeptides, which differ by one amino acid. For HP-gp3, the last hexapeptide is number 89.

As explained above, P-gp is a tandemly duplicated molecule made up of two halves with each encoding for six transmembrane domains and an ATP binding domain. The two halves of P-gp are linked by a linker domain. Of the 90 amino acids that make up the linker domain, 32 amino acid are either positively or negatively charged at physiological pH. While P-gp phosphorylation sites appear to have relevance to P-gp function, the function of the linker domain of P-gp remains unknown. To identify and dissect the role of this domain in MDR, the overlapping peptides method of the present invention was used. A novel approach was developed to isolate interacting proteins using overlapping synthetic hexapeptides. The use of overlapping peptides to isolate interacting proteins allows the specific identification of interacting proteins and bypasses many of the problems associated with the use of random peptides. FIG. 5 shows the amino acid sequences of the linker domain of HP-gp 1 and HP-gp 3. The two linker domains of HP-gp1 and HP-gp3 share 41% amino acid sequence identity and 66% sequence homology. Overlapping hexapeptides were synthesized in parallel on derivatized polypropylene rods as previously described (36, 37). 92 and 90 hexapeptides were synthesized to cover the entire linker sequence of HP-gp1 and HP-gp3, respectively. The hexapeptides remain covalently attached to the polypropylene rods.

To identify the interacting proteins with the various hexapeptides of the linker domains, the peptide-fixed rods were incubated with total cell lysate from [$^{35}$S] methionine metabolically labeled CEM or CEM/VLB$^{1.0}$ cells. After washing off non-specifically binding lysate proteins, the specifically bound proteins were eluted with SDS containing buffers and resolved by SDS-PAGE. FIG. 6 shows the proteins specifically bound to the 92 overlapping hexapeptides from HP-gp1 linker sequence. Three regions in HP-gp1 linker domain ($^{617}$EKGIYFKLVTM$^{627}$ (SEQ ID NO: 1), $^{657}$SRSSLIRKRSTRRSVRGSQA$^{676}$ (SEQ ID NO: 2) and $^{693}$PVSFWRIMKLNLT$^{705}$ SEQ ID NO: 3) bound a 57 kDa protein. The hexapeptides numbers 46–60, 81–89 and 5–9 (see FIG. 5) bound with decreasing affinities to the 57 kDa protein (FIG. 6). Moreover, peptides 46–60 showed binding to two other proteins with apparent molecular masses of 80 kDa and 30 kDa, however much weaker than that of the 57 kDa protein. It is likely that the latter proteins (80 kDa and 30 kDa) are associated with the 57 kDa, since these proteins are detected when the intensity of the 57 kDa protein signal is high (FIG. 6, peptides 50–56). Comparison of the amino acid sequences of the three 57 kDa binding proteins did not reveal significant sequence homology among them to account for their binding to the same protein. Interestingly, however, the amino acid sequence of the second region (peptides 46–60) encodes for protein kinase C consensus sequences (15). In addition, the third region (peptides 81–89) was also shown to encode for a protein kinase A site (43).

Figure 7:
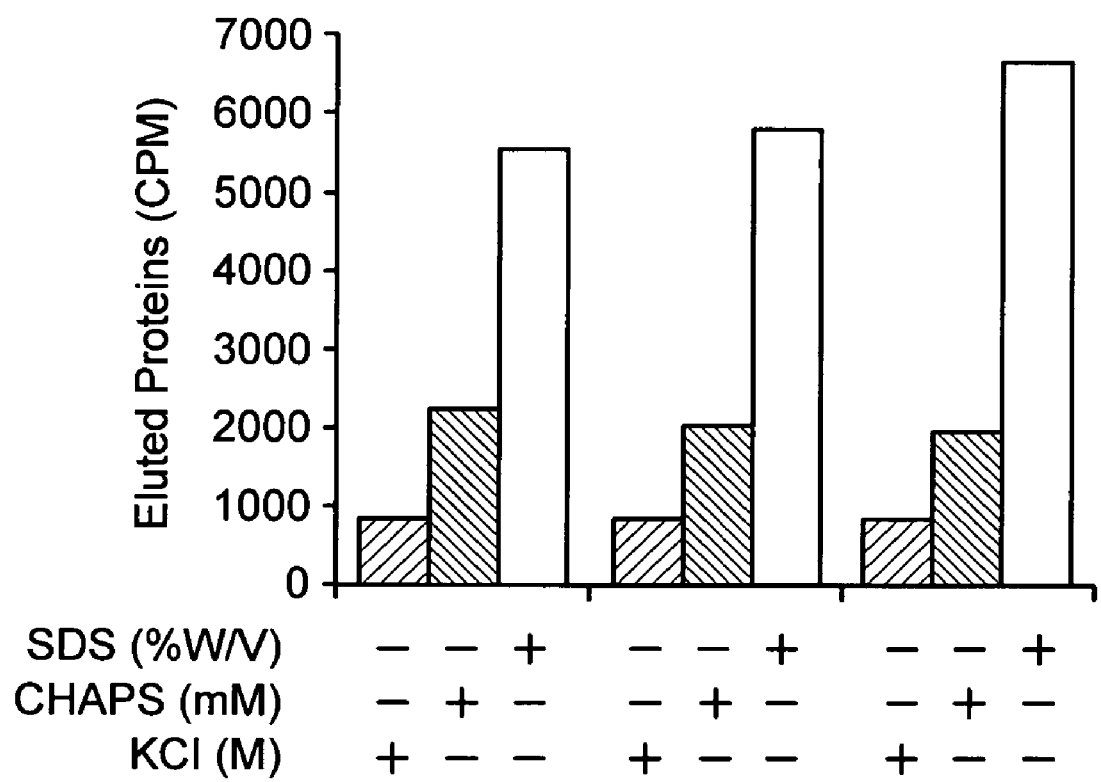
FIG. 7 shows the effects of different detergents or high salt on the binding of proteins to HP-gp1 hexapeptides. Metabolically radiolabeled proteins bound to hexapeptides (hexapeptides 50 to 53) from HP-gp1 linker domain were eluted in the presence of increasing concentrations of anionic detergent (0.12%–0.5% SDS), zwitterionic detergent (20 mM–80 mM CHAPS) or salt (0.3 M–1.2 M KCl). The y-axis represents the amount of radioactivity eluted from a pool of three hexapeptides (50 to 53).
Figure 8:
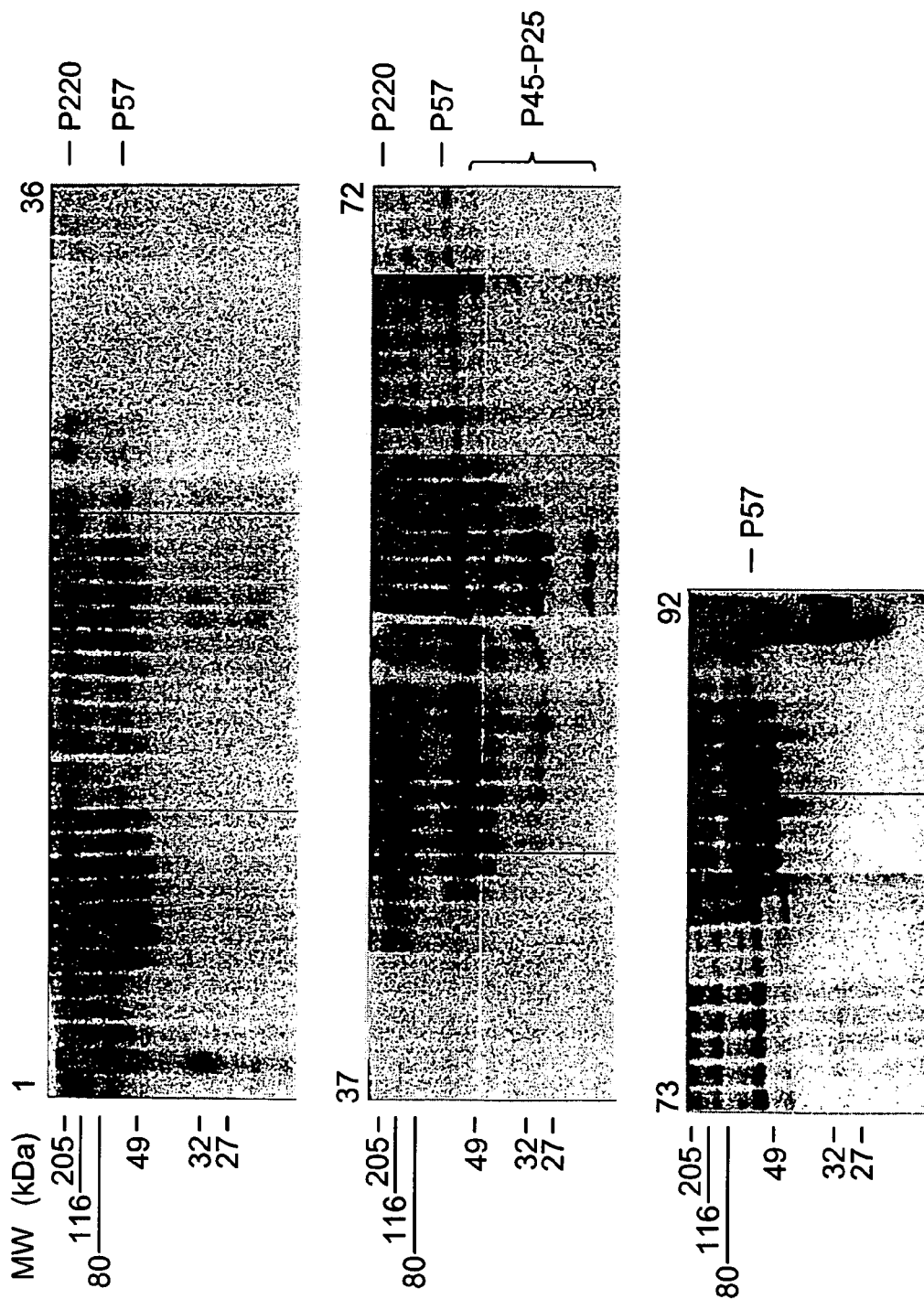
FIG. 8 shows the effects of CHAPS on the binding of proteins to the overlapping hexapeptides encoding HP-gp1 linker domain. Overlapping hexapeptides of the linker domain of HP-gp1 were incubated with total cell lysate from [$^{35}$S] methionine metabolically labeled cells extracted with 10 mM CHAPS. Bound proteins were eluted from the peptide-fixed rods and resolved by 10% SDS-PAGE. Lanes 1 to 92 show the [$^{35}$S] methionine bound proteins to HP-gp1 linker domain. The migration of the molecular weight markers is shown to the left of gels.

To determine the affinity of binding between the sequences of the hexapeptides and the 57 kDa protein, it was of interest to determine the effects of high salt (0.3–2.4 M KCl), zwitterionic detergent (10–160 mM CHAPS) and ionic detergents (0.1%–2% SDS) on the interactions between the hexapeptides encoded by $^{657}$SRSSLIRKRSTRRSVRGSQA$^{676}$ (SEQ ID NO: 2) and the 57 kDa protein. Our results show the binding to be stable to high salt, moderately stable to high concentrations of CHAPS, but sensitive to low concentrations of SDS (FIG. 7). Given the stability of protein binding to covalently attached peptides, in the presence of 10 mM CHAPS, it was of interest to determine the binding of the hexapeptides from HP-gp1 linker domain to CHAPS soluble proteins that could include integral membrane proteins. The results in FIG. 8 show bound proteins to the same overlapping hexapeptides that codes for the linker domain of HP-gp 1. Although the hexapeptides numbers 46–60, 81–89 and 5–9 (see FIG. 5) bound to the 57 kDa protein (FIG. 7); other proteins were found to interact with the same or different hexapeptides which did not bind proteins in the absence of 10 mM CHAPS. For example, hexapeptides 3–10 bound to ~210 kDa protein that was not detected previously in the absence of CHAPS. Similarly, hexapeptides 16–20, which did not bind any proteins in the absence of CHAPS, bound to the same high molecular weight protein (FIG. 7). Peptides 40–60 bound more strongly to several low molecule weight proteins (~45–25 kDa) in the presence of CHAPS. The hexapeptides 80–89 bound to two other proteins in addition to the 57 kDa protein. Taken together, the results in FIG. 8 demonstrate that the binding between the various hexapeptides to the 57 kDa protein is resistant to mild zwitterionic detergents such as CHAPS. Moreover, the solubilization of membrane proteins in 10 mM CHAPS show binding to other proteins not seen in the absence or 10 mM CHAPS. One possibility is that 10 mM CHAPS allows integral membrane proteins to interact with the various hexapeptides of HP-gp 1 linker domain. Alternatively, CHAPS exposes new domains that in turn allows for binding to hexapeptides of HP-gp1 linker domain. In addition, some of the lower molecular weight proteins that bound to hexapeptides 40–60 and 80–89 may be degradation products of the 57 kDa protein (FIG. 8).

Figure 9:
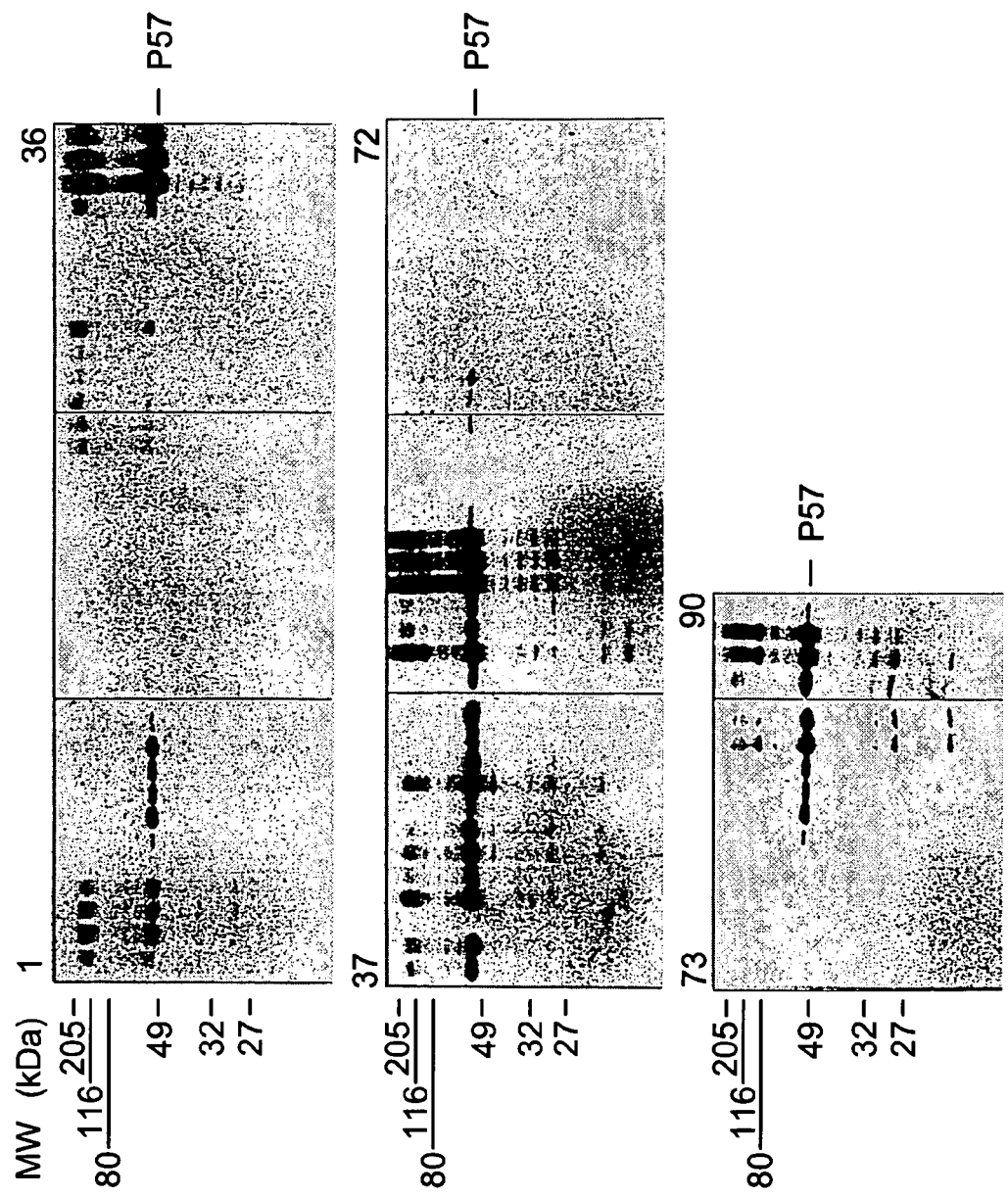
FIG. 9 shows the protein binding to overlapping hexapeptides encoding HP-gp3 linker domain. Overlapping hexapeptides that encode the linker domain of HP-gp3 were synthesized on polypropylene rods and used to identify proteins that bind to these peptides. A total of 88 plus two control hexapeptides for HP-gp3 were incubated with total cell lysate from [$^{35}$S] methionine metabolically labeled cells. All bound proteins were eluted from the peptide-fixed rods and resolved on 10% SDS-PAGE. Lanes 1 to 90 show the [$^{35}$S] methionine bound proteins from HP-gp3. The migration of the molecular weight markers is shown to the left of gels.

The P-gp gene family in man is encoded by two isoforms, HP-gp 1 and HP-gp 3 (or mdr 1 and mdr 3; (20)). However, as indicated earlier, only HP-gp 1 confers an MDR phenotype. Moreover, although HP-gp 1 and 3 share about 80% amino acid sequence homology (111); the linker domain is the most variable domain among the two isoforms with 66% amino acid sequence homology. To determine if the HP-gp 3 linker domain binds to the same or different proteins, overlapping hexapeptides encoding HP-gp 3 linker domain were synthesized on polypropylene rods and their binding to soluble proteins was examined as indicated above. FIG. 9 shows the profile of binding proteins to the hexapeptides of HP-gp 3. Interestingly, a similar molecular weight protein (57 kDa) also bound to the hexapeptides from HP-gp 3. However, the binding to some hexapeptides was different from that seen with HP-gp 1 (FIG. 6 versus FIG. 9). For HP-gp 3, three larger stretches of amino acids ($^{618}$LMKKEG-VYFKLVNM$^{631}$ (SEQ ID NO: 4), $^{648}$KAATRMAPNGWK-SRLFRHSTQKNLKNS$^{674}$ (SEQ ID NO: 5) and $^{695}$PVS-FLKVLKLNKT$^{707}$ (SEQ ID NO: 6) bound to the 57 kDa protein. The first and third regions of HP-gp 3 linker domain share considerable sequence identity with the first and third regions of HP-gp 1 linker domain (FIG. 10). Hence, it is not surprising that the same hexapeptides bound to the same protein. The second region of HP-gp 1 and HP-gp 3 linker domains are different (FIG. 10). Consequently, although both the HP-gp1 and HP-gp3 sequences bound to a 57 kDa, the region of interaction between HP-gp 3 and the 57 kDa protein is larger than that of HP-gp 1 (FIG. 6 and FIG. 9). A comparison of the amino acid sequences from HP-gp 1 and HP-gp 3 binding hexapeptides is shown in FIG. 10.

EXAMPLE 9

Purification and Sequencing of the 57 kDa Protein

Figures 11, 12:
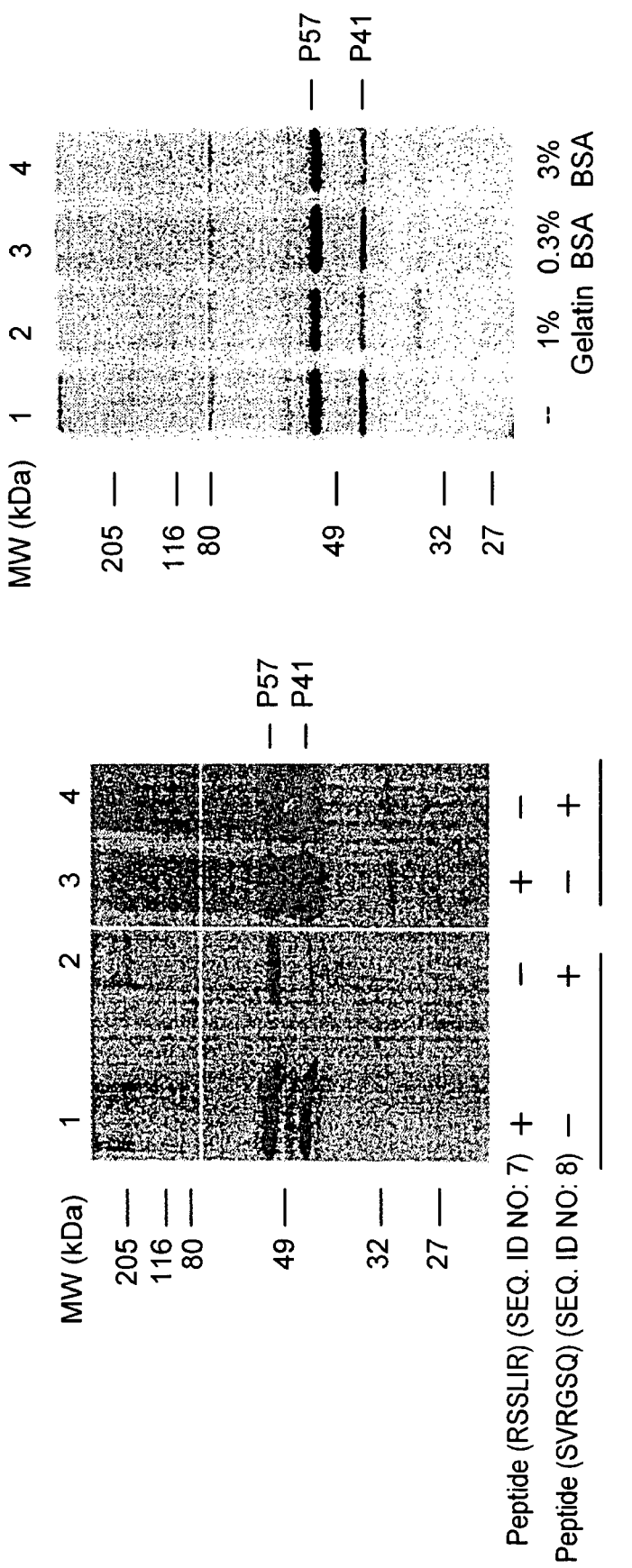
FIG. 11 shows the two high affinity binding hexapeptides. Two high affinity binding sequences $^{658}$RSSLIR$^{663}$ (SEQ ID NO: 7) and $^{669}$SVRGSQ$^{674}$ (SEQ ID NO: 8) from HP-gp1 linker domain were resynthesized and incubated with total cell lysate from [$^{35}$S] methionine metabolically labeled cells following 24 hour or 48 hour incubation times. Bound proteins were eluted from peptide-fixed rods and resolved by 10% SDS-PAGE. The migration of the molecular weight markers is shown to the left of the figure.
FIG. 12 shows the effects of different carrier proteins as blocking agent of unspecific binding. Total cell lysates from [$^{35}$S] methionine metabolically labeled CEM cells were used as is or made 1% gelatin, 0.3% BSA or 3% BSA. The cell lysates were incubated with a high affinity binding hexapeptide $^{658}$RSSLIR$^{663}$ (SEQ ID NO: 7) from HP-gp1 linker domain. The bound proteins were eluted with SDS sample buffer and resolved on 10% SDS-PAGE. The migration of the molecular weight markers is shown to the left of the figure.

To determine the identity of the 57 kDa proteins, several copies of two hexapeptides ($^{658}$RSSLIR$^{663}$ (SEQ ID NO: 7) and $^{669}$SVRGSQ$^{674}$ (SEQ ID NO: 8) from the second region of HP-gp 1 linker domain were synthesized. The latter hexapeptide sequences were those that bound with the highest affinity to the 57 kDa protein. FIG. 11 shows the binding of these two peptides to total cell lysate from [$^{35}$S] methionine metabolically labeled cells. Both hexapeptides bound specifically to the 57 kDa protein and another protein of an apparent molecular mass of ~41 kDa. Interestingly, longer incubation times of the total cell lysate led to an increase in the level of the 41 kDa protein (FIG. 11). Thus, the 41 kDa band is likely a degradation product of the 57 kDa protein.

Figures 13, 14:
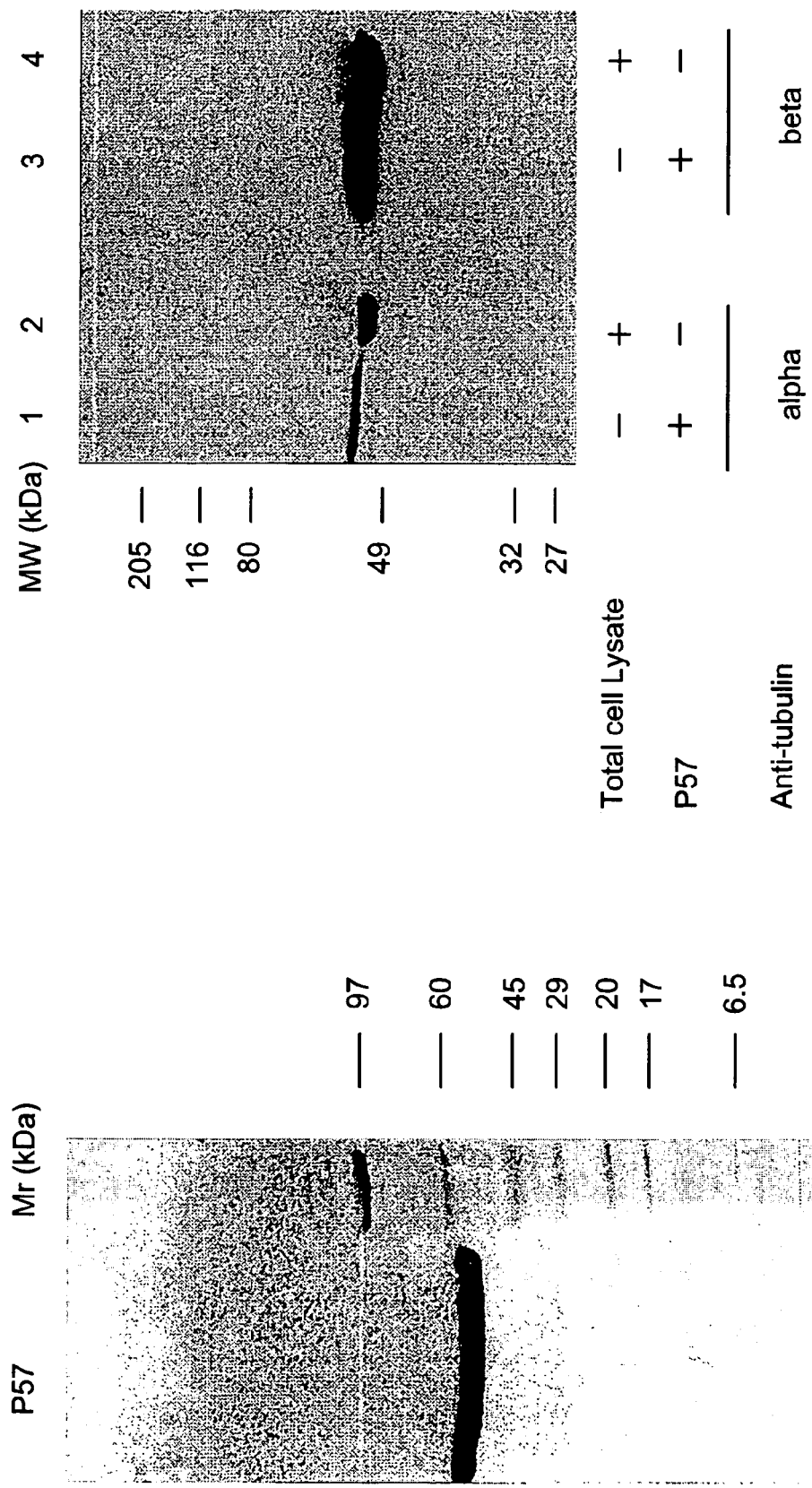
FIG. 13 shows the purification of a 57 kDa protein. Total cell lysate was incubated with fifty HP-gp1 hexapeptides $^{658}$RSSLIR$^{663}$ (SEQ ID NO: 7) and $^{669}$SVRGSQ$^{674}$ (SEQ ID NO: 8). Samples containing the 57 kDa protein (P57) from one hundred hexapeptide incubation mix were pooled and resolved by 10% SDS-PAGE. The resolved proteins were transferred to PVDF membrane and stained with Ponceau S. The migration of the molecular weight markers is shown to the right of the figure.
FIG. 14 shows a Western blot analysis with anti-tubulin monoclonal antibodies. Total cell lysate from CEM cells and proteins eluted from the high affinity binding hexapeptides of HP-gp1 linker domain (P57) were resolved on SDS-PAGE and transferred to nitrocellulose membrane. One half of the membrane was probed with anti-α and anti-β tubulin monoclonal antibodies. The migration of the molecular weight markers is shown to the left of the figure.

To purify the 57 kDa protein using the two hexapeptides, it was of interest to determine if other carrier proteins than BSA can be used. FIG. 12 shows the effects of no blocking carrier, 1% gelatin and 0.3% or 3% BSA on the binding of the hexapeptides to the 57 kDa protein. The results of this experiment were surprising in that no carrier protein was required to reduce the unspecific binding (FIG. 12). The latter established binding conditions were used to isolate large amounts of 57 kDa protein that bound to several copies of hexapeptides $^{658}$RSSLIR$^{663}$ (SEQ ID NO: 7) and $^{669}$SVRGSQ$^{674}$ (SEQ ID NO: 8). FIG. 13 shows purified 57 kDa protein on SDS-PAGE stained with Coomassie blue. The latter purified protein was transferred to PVDF membrane and stained with Ponceau S to localize the position of the 57 kDa protein. The Ponceau S-stained band that migrated with the expected molecular mass was cut out and used for direct N-terminal sequencing (33). The first seven rounds of Edman degradation showed two sequences of MREVISI (SEQ ID NO: 10) and MREIVHI (SEQ ID NO: 11). These two sequences differed only by three amino acids (VIS instead of IVH). Comparison of the two sequence with known protein sequences using FastA protein search engine, showed the latter sequences to encode the first seven N-terminal amino acids of α- and β-tubulins. The identification of tubulins, as the 57 kDa protein was consistent with the apparent molecular mass and the potential degradation products that were observed following long incubation periods. To further confirm the identity of the 57 kDa protein as tubulins, Western blot analysis was performed on hexapeptide-bound 57 kDa protein and total cell lysate resolved by SDS-PAGE and transferred to nitrocellulose membrane. The nitrocellulose membrane was then probed with anti α-tubulin and anti-β-tubulin monoclonal antibodies, respectively. FIG. 14 shows the results of the Western blot analysis. Consistent with the sequencing results, both tubulin subunits (α and β) were recognized in the lanes containing the hexapeptide bound proteins. Thus, establishing the identity of the 57 kDa protein as α and β-tubulin.

EXAMPLE 10

The power of the overlapping peptide spanning method invention was thus validated with P-gp. As shown above, the overlapping peptide-based method of the present invention provides the proof of principle to the hypothesis which states that the region between two interacting proteins consists of high affinity binding sequences and repulsive sequences as well as the fact that such a method can be used efficiently and successfully to identify and characterize domains and sequences of interacting proteins. The balance of high affinity and repulsive forces determine whether two proteins will form stable complex. The use of short overlapping peptides allows the identification of such high affinity binding sequences between bait and prey proteins. The rationale for using short overlapping peptides to isolate high affinity binding sequences is essential to the success and efficiency of the proof of the principle described herein. For instance, larger peptides could contain both high affinity and repulsive binding sequences in one peptide sequence such that the net force of interaction is negative. Moreover, the use of overlapping peptides that differ by one amino acid from the previous or next peptide reduces the possibility of unspecific binding. Thus, overlapping peptides often demonstrate a peak in the binding affinity of various peptides (see FIGS. 7 and 4). The skilled artisan will understand that longer overlapping peptides could also be used. Unfortunately, such larger peptides increase the risk of missing the identification of interacting proteins due to a change in the balance between high affinity and repulsive amino acids.

The binding of 57 kDa protein to three different regions in HP-gp1 and HP-gp3 linker domains is consistent with the herein proposed hypothesis to explain protein interactions (see principle of protein-protein interactions). The high affinity binding domains vary in sizes from 10–26 amino acids in length. In the case of HP-gp1 and HP-gp3 linker domains, two of the three high affinity binding domains shared considerable sequence identity. The third high affinity binding region of the linker domains ($^{658}$SRSS-LIRKRSTRRSVRGSQA$^{677}$ (SEQ ID NO: 2) versus $^{648}$KAATRMAPNGWKSRLFRHSTQKNLKNS$^{674}$ (SEQ ID NO: 5)) shared no homology in their primary amino acid sequence. However, helical wheel presentation of these two domains show a cluster of positively charged residues on one face of the helix while a cluster of serine/threonine residues on the other side (see FIG. 15). Interestingly, the region of highest binding affinity to the 57 kDa protein encodes the three putative phosphorylation sites in HP-gp 1 (15). The positions of the phosphorylation sites in HP-gp3 have not been determined experimentally, however they encode for the consensus sequence of protein kinase C. In this respect, it is possible that HP-gp1 and HP-gp3 interactions as the linker domains is modulated by phosphorylation of this domain. Thus, although mutations of P-gp phosphorylation sites within the linker domain were shown not to affect its drug transport function (40), other proposed functions of HP-gp1 (e.g., regulator of endogenous chloride channel) was shown to be affected by its phosphorylation state (41, 110). Indeed, a member of the ABC transporters, CFTR (the cystic fibrosis transmembrane conductance regulator), which encodes a similar linker domain was found to co-localize with the microtubule network (107). Furthermore, microtubule-dependent acute recruitment of CFTR to the apical plasma membrane of T84 cells was responsive to elevations in intracellular cAMP and phosphorylation of the linker domain (107). Taken together, although it is not clear if phosphorylation plays a role in modulating P-gp functions in a tubulin dependent manner, given the co-localization of HP-gp1 phosphorylation and binding to tubulin, such a possibility is likely. Work is in progress to determine if phosphorylated hexapeptides bind to tubulin using the assay described herein. Thus, the present invention opens the door to the validation of a physiologically relevant interaction between proteinaceous domains.

The possibility that the 57 kDa protein binds to the polypropylene rods or their derivatized moieties is unlikely since all other rods which are similarly derivatized did not bind the 57 kDa protein. Moreover, hexapeptides synthesized on at least four different times bound to the same proteins. Finally, hexapeptides encoding the first and third high affinity binding regions of the linker domains of HP-gp1 and HP-gp3 bound to the 57 kDa protein. In addition to the 57 kDa protein, other proteins with apparent molecular masses of ~80 kDa and 30 kDa also bound to some of the hexapeptides in the linker domains. However, the binding of these proteins was much weaker than the 57 kDa and maybe associated proteins. Although direct measurements of binding affinities between the various hexapeptides and the 57 kDa protein have not been done, it is interesting that this interaction is resistant to 10 mM CHAPS and high salt. Moreover, the presence of 10 mM CHAPS in the incubation mix lead to the binding of other proteins (most notably the ~210 kDa protein) to several stretches of hexapeptides which did not bind in the absence of 10 mM CHAPS. The binding of the latter proteins to the hexapeptides 15–28 are likely due to the extraction of proteins from the membranous material which were excluded in the absence of CHAPS. In absence of CHAPS, the cell lysate contained soluble proteins and membrane associated proteins only.

The physiological significance of HP-gp1 or HP-gp3 binding to tubulin is not clear. However, tubulin has been shown to interact with several membrane proteins (42, 50, 81, 86). HP-gp1 or HP-gp3 interactions with tubulin and possibly microtubules maybe an example of the membrane-skeleton fence model (56). In this model, a small fraction of membrane receptors seem to be fixed to the underlying cytoskeleton (95). It is interesting in this respect that increase in the stability and expression of P-gp in rat liver tumors in vivo are associated with similar increases in the stability of several cytoskeleton proteins, including α-tubulin, β-actin, and cytokeratins 8/18 (64). Work is in progress to determine the functional significance of P-gp interactions with tubulin in vivo.

EXAMPLE 11

The Overlapping Peptides Spanning Method is not Limited to Pgp-Interacting Proteins The overlapping peptide approach of the present invention has been further validated with Annexin I, a soluble and membrane associated protein, as opposed to P-glycoprotein, a strictly transmembrane protein. Annexin is thus structurally and functionally different from P-glycoprotein.

Using this approach, several proteins that interact with Annexin I, and the precise amino acid sequences of Annexin I which mediate these interactions, were identified. Annexin I is a member of a large family of intracellular soluble and membrane associated proteins that bind phospholipids in a reversible and calcium-dependent manner. Various members of the Annexin family have been implicated in a number of different intracellular processes including vesicular trafficking, membrane fusion exocytosis, signal transduction, and ion channel formation and drug resistance. Given the many possible physiological functions of Annexin I, the method of the present invention was set out to identify its interacting proteins and the precise amino acid sequences that mediate Annexin I interactions thereto.

Briefly, as described earlier, overlapping peptides corresponding to the entire amino acid sequence of Annexin I (total of ~340 peptides plus controls) were synthesized on a solid support as described above. In this case, overlapping heptapeptides, as opposed to hexapeptides were used. The peptides were then incubated with total cellular proteins isolated from MCF7 breast tumor cells that were metabolically labeled with [$^{35}$S] methionine. Following several washes, the bound proteins were eluted and resolved on SDS-PAGE as outlined above. The results are consistent with previous results with P-glycoprotein, as the method leads to the identification of several islands of Annexin I amino acid sequences (data not shown) which interacted with five proteins ranging in molecular masses from 10 kDa to 200 kDa (specifically, ~10 kDa; ~29 kDa; ~85 kDa; ~106 kDa and ~200 kDa). Briefly, eight interacting domains having high affinity for the cellular proteins of the extract were identified. Two of these high affinity islands were located in the tail domain of Annexin (residues 1–36) and six in the α helical bundles of Annexin I (residues 37-to the end; see for example WO 99/21980). The identity of the latter interacting proteins is presently under study. However, the interaction of a 10 kDa protein with Annexin I is consistent with earlier works which demonstrated a direct interaction between Annexin I and S100C protein (70).

Thus, the present invention is shown to enable the simple and efficient identification of high affinity protein interaction as well as enabling the simultaneous identification of the precise amino acid sequence of at least one of the interacting partners.

CONCLUSIONS

In conclusion, a simple approach to identify P-gp interacting proteins from a total cell lysate has been used. Moreover, this approach allows for the identification of the precise amino acid sequences in P-gp1 and P-gp3 linker domains that mediate the protein interactions with tubulins. In addition, knowledge of the high affinity binding sequences allow for the subsequent purification of the interacting proteins from a total mixture of cellular proteins, as further exemplified with Annexin I. Indeed, given the simplicity of this approach to study protein-protein interactions, it is easily applied to other proteins. Finally, our approach is rapid and has several advantages over other currently used approaches.

Although the present invention has been described hereinabove by way of preferred embodiments thereof, it can be modified, without departing from the spirit and nature of the subject invention as defined in the appended claims.

REFERENCES

1. Adorini, L., 1993, Clin Exp Rheumatol 8:S41–44.
2. Ahmad et al., 1994, Biochemistry 33:10313–10318.
3. Alba et al., 1998, Electrophoresis 19:2407–2411.
4. Ausubel, et al., 1994, Current Protocols in Molecular Biology, Wiley, New York.
5. Bates et al., 1995, Cancer Chemotherapy & Pharmacology. 35:457–463.
6. Bates et al., 1992, Biochemistry 31:6366–6372.
7. Bates et al., 1993, Biochemistry 37:9156–9164.
8. Beck, W. T., 1983, Cancer Treat. Rep. 67:875–882.
9. Boscoboinik et al., 1990, Biochimica et Biophysica Acta 1027:225–228.
10. Brown et al., Nat Genet. 1999 Jan;21(1 Suppl):33-7, Review.
11. Buschman et al., 1994, Cancer Research 54:4892–4898.
12. Campbell, et al., 1984, Monoclonal Antibody Technology: Laboratory Techniques in Biochemistry and Molecular Biology, Elsevier Science (Publ.), Amsterdam, The Netherlands.
13. Chambers et al., 1990, Biochemical and Biophysical Research Communications 169:253–259.
14. Chambers et al., 1994, Biochemical Journal 299:309–315.
15. Chambers et al., 1993, The Journal of Biological Chemistry 268:4592–4595.
16. Chan et al., 1995, Hematology—Oncology Clinics of North America 9:275–318.
17. Chan et al., 1991, New England Journal of Medicine 325:1608–1614.
18. Chen et al., 1997, Curr Opin Chem Biol 1:458–466.
19. Cheung et al., Nat Genet. 1999 Jan;21(1 Suppl):15-9, Review.
20. Childs et al., 1994, Important Adv Oncol, 21–36.
21. Cole et al., 1996, Cancer Treatment & Research 87:39–62.
22. Cornelissen et al., 1994, Journal of Clinical Oncology 12:115–119.
23. Dalton et al., 1995, Cancer 75:815–820.
24. Debouck et al., Nat. Genet. 1999 Jan;21(1 Suppl):48–50, Review.
25. Devault et al., 1990, Molecular and Cellular Biology 10:1652–1663.
26. Duggan et al., Nat Genet. 1999 Jan;21(1 Suppl):10-4, Review
27. Edman et al., 1967, Eur J Biochem 1:80–91.
28. Ehrmann et al., 1997, Neoplasma 44:299–304.
29. Felder et al., 1993, Mol Cell Biol 13:1449–1455.
30. Fields et al., 1994, Trends Genet 10:286–292.
31. Fine et al., 1988, Proceedings of the National Academy of Science USA 85:582–586.
32. Fitscher et al., 1993, Analytical Biochemistry 213:414–421.
33. Flynn et al., 1983, Biochem Biophys Res Commun 117:859–65.
34. Ford et al., 1990, Pharmacological Reviews 42:155–199.
35. Futscher et al., 1993, Analytical Biochemistry 213:414–421.
36. Georges et al., 1993, The Journal of Biological Chemistry 268:1792–1798.
37. Georges et al., 1990, Proceedings of the National Academy of Science USA 87:152–156.
38. Georges et al., 1990, Advances in Pharmacology 21:185–220.
39. Georges et al., 1991, Journal of Cellular Physiology 148:479–484.
40. Germann et al., 1996, J Biol Chem 271:1708–16.
41. Gill et al., 1992, Cell 71:23–32.
42. Giustetto et al., J Comp Neurol 395:231–244.
43. Glavy et al., 1997, J Biol Chem 272:5909–5914.
44. Goldstein, L. J., 1995, Curr Probl Cancer 19:65–124.
45. Gottesman et al., 1995, Annu Rev Genet 29:607–649.
46. Gottesman et al., 1993, Annual Review of Biochemistry 62:385–427.
47. Grogan et al., 1990, Laboratory Investigation 63:815–824.
48. Gros et al., 1986, Cell 47:371–380.
49. Gupta, S., 1996, "P-glycoprotein Expression in Normal Hematopoietic Progenitors and Cells of the Immune System" in *Multidrug Resistance in Cancer Cells: Molecular, Biochemical, Physiological and Biological Aspects*. Editors: Gupta, S. and Tsuruo, T., John Wiley & Sons, NY., 293–302.
50. Haga et al., 1988, Eur J Biochem 255:363–368.
51. Hardy et al., 1995, The EMBO Journal 14:68–75.
52. Heldin, C. H., 1995, Cell 80:213–223.
53. Herweijer et al., 1990, Journal of the National Cancer Institute 82:1133–1140.
54. Higgins C. F., 1992, Annual Review of Cell Biology 8:67–113.
55. Hoogenboom et al., 1998, Immunotechnology 4:1–20.
56. Jacobson et al., 1995, Sciences 268:1441–1442.
57. Jolliet-Riant et al., 1999, Fundam Clin Pharmacol 13:16–26.
58. Kast et al., 1997, J. Biological Chemistry 272:26479–26487.
59. Klemm et al., 1998, Annu Rev Immunol 16:569–592.
60. Klotz et al., 1975, In H. Neurath and R. L. Hill (ed.), The Proteins, Academic Press, Inc. New York:293–411.
61. Kuriyan et al., 1997, Annu Rev Biophys Biomol Struct 26:259–288.
62. Laemmli, U. K., 1970, Nature 227:680–685.
63. Landschulz et al., 1988, Science 240:1759–1764.
64. Lee et al., 1998, J Cell Physiol 177:1–12.
65. Li et al., 1993, Nature 363:85–88.
66. Ling, V., 1997, Cancer Chemother Pharmacol 40:Suppl: S3–8.
67. List et al., 1993, Journal of Clinical Oncology 11:1652–1660.
68. Loo et al., 1995, The Journal of Biological Chemistry 270:843–848.
69. Lowry et al., 1951, Journal of Biological Chemistry 193:265–275.

70. Mailliard, W. S., et al., 1996, The Journal of Biological Chemistry, 271:719–725.
71. Martini et al., 1998, Curr Opin Neurol 11:545–556.
72. McCoy et al., 1997, EMBO J 16:6230–6236.
73. Miller, et al., 1988, Ann. Reports Med. Chem. 23:295.
74. Molina et al., 1996, Pept Res 9:151–155.
75. Morgan, et al., 1987, Nucleic Acids Research, 14:5019.
76. Naito et al., 1992, Biochemical and Biophysical Research Communications 185:284–290.
77. Nare et al., 1994, Biochemical Pharmacology 48:2215–2222.
78. Nooter et al., 1994, Leukemia Research 18:233–243.
79. O'Brien et al., 1996, "P-glycoprotein Expression in Normal Human Tissues," in *Multidrug Resistance in Cancer Cells: Molecular, Biochemical, Physiological and Biological Aspects*. Editors: Gupta, S. and Tsuruo, T., John Wiley & Sons, NY., 285–292.
80. Pawson et al., 1992, Cell 71:359–362.
81. Perrot-Applanat et al., 1995, J Cell Sci 108:2037–2051.
82. Phizicky et al., 1995, Microbiological Reviews 59:94–123.
83. Porpaczy et al., 1983, Biochem. Biophysica. Acta. 749:172–179.
84. Prelich et al., 1989, Nature 326:517–520.
85. Ramsay et al., Nat Biotechnol. 1998 Jan;16(1):40–4, Review.
86. Ravindra, R., 1997, Endocrine 7:127–143.
87. Reed et al., 1996, J Cell Biochem 60: 23–32.
88. Remington, Pharmaceutical Science, 16$^{th}$ Edition, Mack, Ed.
89. Ro et al., 1990, Human Pathology. 21:787–791.
90. Roninson et al., 1986, Proceedings of the National Academy of Sciences USA 83:4538–4542.
91. Rosenberg et al., 1997, Journal of Biological Chemistry. 272:10685–10694.
92. Ruetz et al., 1994, The Journal of Biological Chemistry 269:12277–12284.
93. Safa et al., 1986, The Journal of Biological Chemistry 261:6137–6140.
94. Safa, A. R., 1993, Cancer Investigation 11:46–56.
95. Sako et al., 1995, J Cell Biol 129:1559–1574.
96. Sambrook, et al., 1989, Molecular Cloning-A Laboratory Manual, Cold Spring Harbor Laboratories.
97. Schena et al., Trends Biotechnol. 1998 Jul;16(7):301–6, Review
98. Schinkel et al., 1991, Cancer Research 51:2628–2635.
99. Schinkel et al., 1994, Cell 77:491–502.
100. Smit et al., 1993, Cell 75:451–462.
101. Sonneveld et al., 1994, Journal Clinical Oncology 12:1584–91.
102. Stanfield et al., 1995, Curr Opin Struct Biol 5:103–113.
103. Stefanou et al., 1998, Anticancer Res 18:4673–4681.
104. Steitz et al., 1977, J Biol Chem 252:4494–4500.
105. Stevenson et al., 1998, Anal Biochem 262:99–109.
106. Susskind et al., 1983, In R. W. Hendrix, J. W. Roberts, F. W. Stahl, and R. A. Weisberg (ed.), Lambda II. Cold Spring Harbor Laboratory Press, Cold Spring Harbor, N.Y.:347–363.
107. Tousson et al., 1996, J Cell Sci 109:1325–34.
108. Towbin et al., 1979, Proceedings of the National Academy of Sciences of the United States of America 76:4350–4354.
109. Tschesche et al., 1975, Eur J Biochem 58:439–451.
110. Valverde et al., 1992, Nature 355:830–833.
111. Van der Bliek et al., 1987, The EMBO Journal 6:3325–3331.
112. Venter et al., 1998, Science 280:1540–1542.
113. Verrelle et al., 1991, Journal of the National Cancer Institute 83:111–116.
114. Vincent et al., 1972, Biochemistry 11:2967–2977.
115. Watanabe et al., 1995, Acta Oncologica 34:235–241.
116. Weinstein et al., 1990, Human Pathology. 21:34–48.
117. Wigler, P. W., 1996, J Bioenerg Biomembr 28:279–84.
118. Wilson et al., 1995, Methods Enzymol 250:79–91.
119. EP-A-0818467
120. WO 98 15833A
121. WO 84 03564A

---

What is claimed is:

1. A method for identifying a polypeptide that binds with a high affinity to a peptide region in a chosen protein, the peptide region being adjacent to a repulsive peptide region of the chosen protein, the method comprising:
   (a) providing a set of short overlapping peptides spanning a complete sequence of at least a domain of the chosen protein, the set of short overlapping peptides being covalently attached to a support;
   (b) contacting the support to which the overlapping peptides are covalently attached with a mixture of polypeptides under conditions enabling binding between the peptides on the support and a polypeptide of the mixture;
   (c) washing the support to remove unbound polypeptides of the mixture;
   (d) identifying a first set of contiguous overlapping peptides that bind the polypeptide, the first set comprising a first region that binds to the polypeptide with a high affinity;
   (e) identifying a second set of contiguous overlapping peptides that bind the polypeptide, the second set comprising a second region that binds to the polypeptide with a high affinity, the second set being discontinuous from the first set; and
   (f) identifying the segment between the first set and the second set, the segment comprising the repulsive peptide region of the chosen protein, the repulsive peptide region being adjacent to the high affinity peptide regions,
   the polypeptide that binds to the first peptide region and the second peptide region being the polypeptide that binds with a high affinity to the peptide region that is adjacent to the repulsive peptide region of the chosen protein.

2. The method of claim 1, wherein the support is selected from the group consisting of a chip, a bead, and a plate.

3. The method of claim 1, wherein the overlapping peptides attached to the support are synthesized synthetically using the amino acid sequence of the chosen protein.

4. The method of claim 1, wherein each of the overlapping peptides attached to the support is from about 5 amino acids to about 15 amino acids in length.

5. The method of claim 1, wherein each of the overlapping peptides attached to the support is from about 5 amino acids to about 12 amino acids in length.

6. The method of claim 1, wherein each of the overlapping peptides attached to the support is from about 5 amino acids to about 10 amino acids in length.

7. The method of claim 1, wherein each of the overlapping peptides attached to the support is from about 5 amino acids to about 7 amino acids in length.

8. The method of claim 1, wherein the mixture of polypeptides comprises a cell lysate.

9. The method of claim 1, wherein the chosen protein is human P-glycoprotein 1.

10. The method of claim 9, wherein the polypeptide is tubulin.

11. The method of claim 1, wherein the chosen protein is human P-glycoprotein 3.

12. The method of claim 1, wherein identifying the polypeptide that is retained on the support is accomplished by a method selected from the group consisting of performing a Western blot, labeling the polypeptide and identifying the labeled polypeptide, mass spectrometry, 2-D gel electrophoresis, and combinations thereof.

13. A method for identifying a peptide region in a chosen protein that binds to a polypeptide with a high affinity and is adjacent to a repulsive peptide region of the chosen protein, the method comprising:
   (a) providing a set of short overlapping peptides spanning a complete sequence of at least a domain of the chosen protein, the set of short overlapping peptides being covalently attached to a support;
   (b) contacting the support to which the overlapping peptides are attached with the polypeptide under conditions enabling binding between the peptide attached to the support and the polypeptide;
   (c) washing the support to remove unbound polypeptide;
   (d) identifying a first set of contiguous overlapping peptides that bind the polypeptide, the first set comprising a first region that binds to the polypeptide with a high affinity;
   (e) identifying a second set of contiguous overlapping peptides that bind the polypeptide, the second set comprising a second region that binds to the polypeptide with a high affinity, the second set being discontinuous from the first set; and
   (f) identifying the segment between the first set and the second set, the segment comprising the repulsive peptide region of the chosen protein, the repulsive peptide region being adjacent to the high affinity peptide regions,
   thereby identifying the peptide region in the chosen protein that binds to a polypeptide with a high affinity and is adjacent to the repulsive peptide region.

14. The method of claim 13, wherein the support is selected from the group consisting of a chip, a bead, and a plate.

15. The method of claim 13, wherein the overlapping peptides attached to the support are synthesized synthetically using the amino acid sequence of the chosen protein.

16. The method of claim 13, wherein each of the overlapping peptides attached to the support is from about 5 amino acids to about 15 amino acids in length.

17. The method of claim 13, wherein each of the overlapping peptides attached to the support is from about 5 amino acids to about 12 amino acids in length.

18. The method of claim 13, wherein each of the overlapping peptides attached to the support is from about 5 amino acids to about 10 amino acids in length.

19. The method of claim 13, wherein each of the overlapping peptides attached to the support is from about 5 amino acids to about 7 amino acids in length.

20. The method of claim 13, wherein the chosen protein is human P-glycoprotein 1.

21. The method of claim 20, wherein the polypeptide is tubulin.

22. The method of claim 13, wherein the chosen protein is human P-glycoprotein 3.

23. The method of claim 13, further comprising identifying the peptide in the chosen protein to which the polypeptide binds the chosen protein.

24. The method of claim 23, wherein the peptide in the chosen protein to which the polypeptide binds is identified by its position on the support.

* * * * *

SEQUENCE LISTING

<160> NUMBER OF SEQ ID NOS: 8

<210> SEQ ID NO 1
<211> LENGTH: 11
<212> TYPE: PRT
<213> ORGANISM: Homo sapiens

<400> SEQUENCE: 1

Glu Lys Gly Ile Tyr Phe Lys Leu Val Thr Met
 1               5                  10

<210> SEQ ID NO 2
<211> LENGTH: 20
<212> TYPE: PRT
<213> ORGANISM: Homo sapiens

<400> SEQUENCE: 2

Ser Arg Ser Ser Leu Ile Arg Lys Arg Ser Thr Arg Arg Ser Val Arg
 1               5                  10                  15

Gly Ser Gln Ala
             20

```
<210> SEQ ID NO 3
<211> LENGTH: 13
<212> TYPE: PRT
<213> ORGANISM: Homo sapiens

<400> SEQUENCE: 3

Pro Val Ser Phe Trp Arg Ile Met Lys Leu Asn Leu Thr
 1               5                  10

<210> SEQ ID NO 4
<211> LENGTH: 14
<212> TYPE: PRT
<213> ORGANISM: Homo sapiens

<400> SEQUENCE: 4

Leu Met Lys Lys Glu Gly Val Tyr Phe Lys Leu Val Asn Met
 1               5                  10

<210> SEQ ID NO 5
<211> LENGTH: 27
<212> TYPE: PRT
<213> ORGANISM: Homo sapiens

<400> SEQUENCE: 5

Lys Ala Ala Thr Arg Met Ala Pro Asn Gly Trp Lys Ser Arg Leu Phe
 1               5                  10                  15

Arg His Ser Thr Gln Lys Asn Leu Lys Asn Ser
             20                  25

<210> SEQ ID NO 6
<211> LENGTH: 13
<212> TYPE: PRT
<213> ORGANISM: Homo sapiens

<400> SEQUENCE: 6

Pro Val Ser Phe Leu Lys Val Leu Lys Leu Asn Lys Thr
 1               5                  10

<210> SEQ ID NO 7
<211> LENGTH: 6
<212> TYPE: PRT
<213> ORGANISM: Homo sapiens

<400> SEQUENCE: 7

Arg Ser Ser Leu Ile Arg
 1               5

<210> SEQ ID NO 8
<211> LENGTH: 6
<212> TYPE: PRT
<213> ORGANISM: Homo sapiens

<400> SEQUENCE: 8

Ser Val Arg Gly Ser Gln
 1               5
```